United States Patent
Szczerba

(10) Patent No.: US 11,077,844 B2
(45) Date of Patent: Aug. 3, 2021

(54) SYSTEM AND METHOD FOR INCREASING PASSENGER SATISFACTION IN A VEHICLE HAVING AN AUTOMATED DRIVING SYSTEM

(71) Applicant: GM GLOBAL TECHNOLOGY OPERATIONS LLC, Detroit, MI (US)

(72) Inventor: Joseph F. Szczerba, Grand Blanc, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 112 days.

(21) Appl. No.: 16/389,330

(22) Filed: Apr. 19, 2019

(65) Prior Publication Data

US 2020/0331481 A1 Oct. 22, 2020

(51) Int. Cl.
*B60W 30/02* (2012.01)
*B60W 40/08* (2012.01)
(Continued)

(52) U.S. Cl.
CPC ....... *B60W 30/025* (2013.01); *A61B 5/02055* (2013.01); *A61B 5/18* (2013.01); *B60W 40/08* (2013.01); *B60W 50/0098* (2013.01); *B60W 50/14* (2013.01); *G05D 1/0088* (2013.01); *G06K 9/00845* (2013.01); *A61B 5/0077* (2013.01); *A61B 5/01* (2013.01); *A61B 5/02438* (2013.01); *A61B 5/0533* (2013.01); *A61B 5/1123* (2013.01); *A61B 5/1128* (2013.01); *A61B 5/681* (2013.01); *A61B 5/6803* (2013.01); *A61B 5/6893* (2013.01); *B60R 1/00* (2013.01); *B60W 2050/146* (2013.01); *B60W 2420/42* (2013.01);
(Continued)

(58) Field of Classification Search
CPC .............. B60W 30/025; B60W 40/08; B60W 2754/30; B60W 2720/106; B60W 2420/42; A61B 5/18; A61B 5/02055; A61B 5/02438; A61B 5/01; A61B 5/0533; A61B 5/681; A61B 5/6803; A61B 5/6893; A61B 5/1123; A61B 5/0077; A61B 5/1128; G05D 1/0088; B60R 1/00
See application file for complete search history.

(56) References Cited

U.S. PATENT DOCUMENTS

2010/0292886 A1* 11/2010 Szczerba ............... G01S 13/723
701/31.4
2018/0365740 A1 12/2018 Nix et al.
(Continued)

*Primary Examiner* — Quan-Zhen Wang
*Assistant Examiner* — Rajsheed O Black-Childress
(74) *Attorney, Agent, or Firm* — Cantor Colburn LLP

(57) ABSTRACT

A system for increasing satisfaction of a passenger in a vehicle having an automated driving system structured to operate the autonomous vehicle may include a first sensor structured to detect a driving environment of the vehicle, the first sensor being operably coupled to the automated driving system; a processor operably coupled to the first sensor and the automated driving system, the processor being structured to calculate a vehicle path plan based on the driving environment of the vehicle and local infrastructure information; and a display operably coupled to the first sensor, the processor, and the automated driving system. The processor may be structured to control the display to display a graphical representation of the driving environment of the vehicle and the vehicle path plan.

18 Claims, 39 Drawing Sheets

(51) Int. Cl.
    *A61B 5/18*     (2006.01)
    *A61B 5/0205*     (2006.01)
    *G05D 1/00*     (2006.01)
    *B60W 50/00*     (2006.01)
    *B60W 50/14*     (2020.01)
    *G06K 9/00*     (2006.01)
    *A61B 5/00*     (2006.01)
    *B60R 1/00*     (2006.01)
    *A61B 5/0533*     (2021.01)
    *A61B 5/01*     (2006.01)
    *A61B 5/024*     (2006.01)
    *A61B 5/11*     (2006.01)

(52) U.S. Cl.
    CPC ... *B60W 2720/106* (2013.01); *B60W 2754/30* (2020.02)

(56) References Cited

U.S. PATENT DOCUMENTS

| | | | |
|---|---|---|---|
| 2019/0225232 A1 | 7/2019 | Blau | |
| 2019/0325219 A1* | 10/2019 | Lin | G06K 9/00832 |
| 2020/0064142 A1* | 2/2020 | Choi | G01C 21/3647 |
| 2020/0125989 A1* | 4/2020 | Sucan | B60W 60/00253 |
| 2020/0272160 A1* | 8/2020 | Djuric | G06T 7/73 |

\* cited by examiner

SYSTEM AND METHOD FOR INCREASING PASSENGER SATISFACTION IN A VEHICLE HAVING AN AUTOMATED DRIVING SYSTEM

INTRODUCTION

The subject disclosure relates to systems and methods for measuring passenger satisfaction in an autonomous vehicle, increasing passenger satisfaction in an autonomous vehicle, and adjusting driving behavior of an autonomous vehicle based on passenger satisfaction.

Developments in autonomous vehicle technology may allow greater access to autonomous vehicles by the public. However, as with many new technologies, there may initially be a lack of trust by passengers in the driving capabilities of autonomous vehicles. Additionally, passengers may become frustrated by the driving operation of an autonomous vehicle, especially if the passenger is unaware of the data with which the autonomous vehicle is making decisions. These issues of lack of trust, lack of satisfaction, and passenger frustration may delay adoption of autonomous vehicle technology by the public. Additionally, present methods of studying passenger satisfaction in autonomous vehicles may rely on subjective assessment of passenger satisfaction after the ride is completed, which may not accurately assess passenger satisfaction and may result in delays in implementing improvements to the driving operation of the autonomous vehicle.

Accordingly, it may be desirable to provide a system and method that can accurately assess passenger satisfaction in an autonomous vehicle in real time as the passenger's reactions occur by detecting objective measures of the passenger's behavior. Further, it may be desirable to provide a system and method that can automatically modify driving behavior of the autonomous vehicle in response to the real-time assessment of passenger satisfaction. Additionally, it may be desirable to provide a method and system for improving passenger satisfaction through modification of driving behavior and presentation of relevant information in a format that is easily understandable by passengers.

SUMMARY

In one exemplary embodiment, a system for increasing satisfaction of a passenger in a vehicle having an automated driving system structured to operate the autonomous vehicle may include a first sensor structured to detect a driving environment of the vehicle, the first sensor being operably coupled to the automated driving system. The system may further include a processor operably coupled to the first sensor and the automated driving system, the processor being structured to calculate a vehicle path plan based on the driving environment of the vehicle and local infrastructure information. The system may further include a display operably coupled to the first sensor, the processor, and the automated driving system. The processor may be structured to control the display to display a graphical representation of the driving environment of the vehicle and the vehicle path plan.

In another exemplary embodiment of the system, the graphical representation may include a current speed of the vehicle, an acceleration status of the vehicle, an indication of nearby objects, and the local infrastructure information.

In another exemplary embodiment of the system, the graphical representation may include an indication of an upcoming maneuver based on the vehicle path plan.

In another exemplary embodiment of the system, the system may further include a communication node structured to communicate with an external device. The communication node may be operably coupled to the processor. The communication node may be structured to receive the local infrastructure information from the external device.

In another exemplary embodiment of the system, the first sensor may include a LIDAR system, and the processor may be structured to control the display to display a thumbnail of an output of the LIDAR system.

In another exemplary embodiment of the system, the processor may be structured to control the display to display an enlarged view of the output LIDAR system in response to an input from the passenger.

In another exemplary embodiment of the system, the system may include a second sensor structured to detect a first property of the passenger, the second sensor being operably connected to the processor. The processor may be structured to calculate a passenger satisfaction index based on the first property of the passenger. The processor may be structured to control the automated driving system to modify driving behavior of the autonomous vehicle in response to the passenger satisfaction index satisfying a first condition. The processor may be structured to control the display to notify the passenger of a change in driving behavior of the vehicle.

In another exemplary embodiment of the system, the first condition may include a predetermined level of passenger dissatisfaction. The processor may be structured to, in response to the passenger satisfaction index satisfying the predetermined level of passenger dissatisfaction, control the automated driving system to increase deliberateness of the driving behavior of the autonomous vehicle.

In another exemplary embodiment of the system, the first property may include a passenger frustration index $I_F$ or a passenger trust index $I_T$.

In another exemplary embodiment of the system, the passenger frustration index $I_F$ may be a function of a road monitoring duration value, a secondary activity duration value, a multi-task activity transaction value, a side window glance value, or a facial gesture value.

In another exemplary embodiment of the system, the passenger frustration index $I_F$ may be a function of a galvanic skin response value, a skin temperature value, a verbal valence value, or a facial gesture value.

In another exemplary embodiment of the system, the system may include a communication node structured to communicate with an external device. The communication node may be operably coupled to the processor. The second sensor may be a smart device worn by the passenger. The communication node may be structured to communicate with the smart device to receive the first property. The first property may include a passenger galvanic skin response, a passenger skin temperature, or a passenger heart rate.

In another exemplary embodiment of the system, the system may include a communication node structured to communicate with an external device. The communication node may be operably coupled to the processor. The communication node may be structured to receive traffic data, weather data, passenger social data, passenger calendar data, or destination data from the external device. The processor may be structured to modify the passenger satisfaction index based on the traffic data, the weather data, the passenger social data, the passenger calendar data, or the destination data.

In an exemplary embodiment, a method for increasing satisfaction of a passenger in a vehicle having an automated driving system structured to operate the autonomous vehicle, may include detecting, with a first sensor, a driving environment of the vehicle. The method may further include obtaining local infrastructure information. The method may further include calculating, with a processor, a vehicle path plan based on the driving environment of the vehicle and the local infrastructure information. The method may further include displaying, on a display, a graphical representation of the driving environment of the vehicle and the vehicle path plan.

In another exemplary embodiment of the method, the displaying a graphical representation may include displaying a current speed of the vehicle, an acceleration status of the vehicle, an indication of nearby objects, and the local infrastructure information.

In another exemplary embodiment of the method, the displaying the graphical representation may include indicating an upcoming maneuver based on the vehicle path plan.

In another exemplary embodiment of the method, the method may further include detecting, with a second sensor, a first property of the passenger. The method may further include calculating, with the processor, a passenger satisfaction index based on the first property of the passenger. The method may further include controlling the automated driving system to modify driving behavior of the autonomous vehicle in response to the passenger satisfaction index satisfying a first condition. The method may further include displaying, on the display, a notification of a change in driving behavior of the vehicle.

In another exemplary embodiment of the method, the first condition may include a predetermined level of passenger dissatisfaction. The method may further include, in response to the passenger satisfaction index satisfying the predetermined level of dissatisfaction, controlling the automated driving system to increase deliberateness of the driving behavior of the vehicle.

In another exemplary embodiment of the method, the method may further include communicating with the second sensor via a communication node of the autonomous vehicle. The second sensor may include a smart device worn by the passenger. The first condition may include a passenger galvanic skin response, a passenger skin temperature, or a passenger heart rate.

In another exemplary embodiment of the method, the method may further include receiving, via a communication node of the autonomous vehicle, traffic data, weather data, passenger social data, passenger calendar data, or destination data from an external device. The passenger satisfaction index may be modified based on the traffic data, the weather data, the passenger social data, the passenger calendar data, or the destination data.

The above features and advantages, and other features and advantages of the disclosure are readily apparent from the following detailed description when taken in connection with the accompanying drawings.

BRIEF DESCRIPTION OF THE DRAWINGS

Other features, advantages and details appear, by way of example only, in the following detailed description, the detailed description referring to the drawings in which.

DETAILED DESCRIPTION

Figure 1:
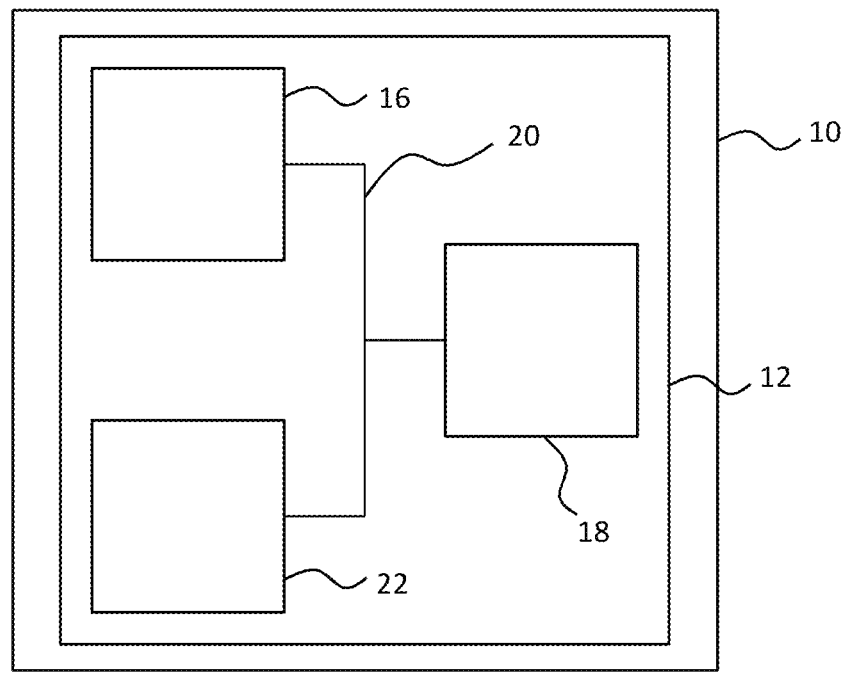
FIG. 1 is a schematic diagram illustrating an exemplary embodiment of a system for measuring passenger satisfaction.

The following description is merely exemplary in nature and is not intended to limit the present disclosure, its application or uses. It should be understood that throughout the drawings, corresponding reference numerals indicate like or corresponding parts and features. As used herein, the term module refers to processing circuitry that may include an application specific integrated circuit (ASIC), an electronic circuit, a processor (shared, dedicated, or group) and memory that executes one or more software or firmware programs, a combinational logic circuit, and/or other suitable components that provide the described functionality.

Figure 2:
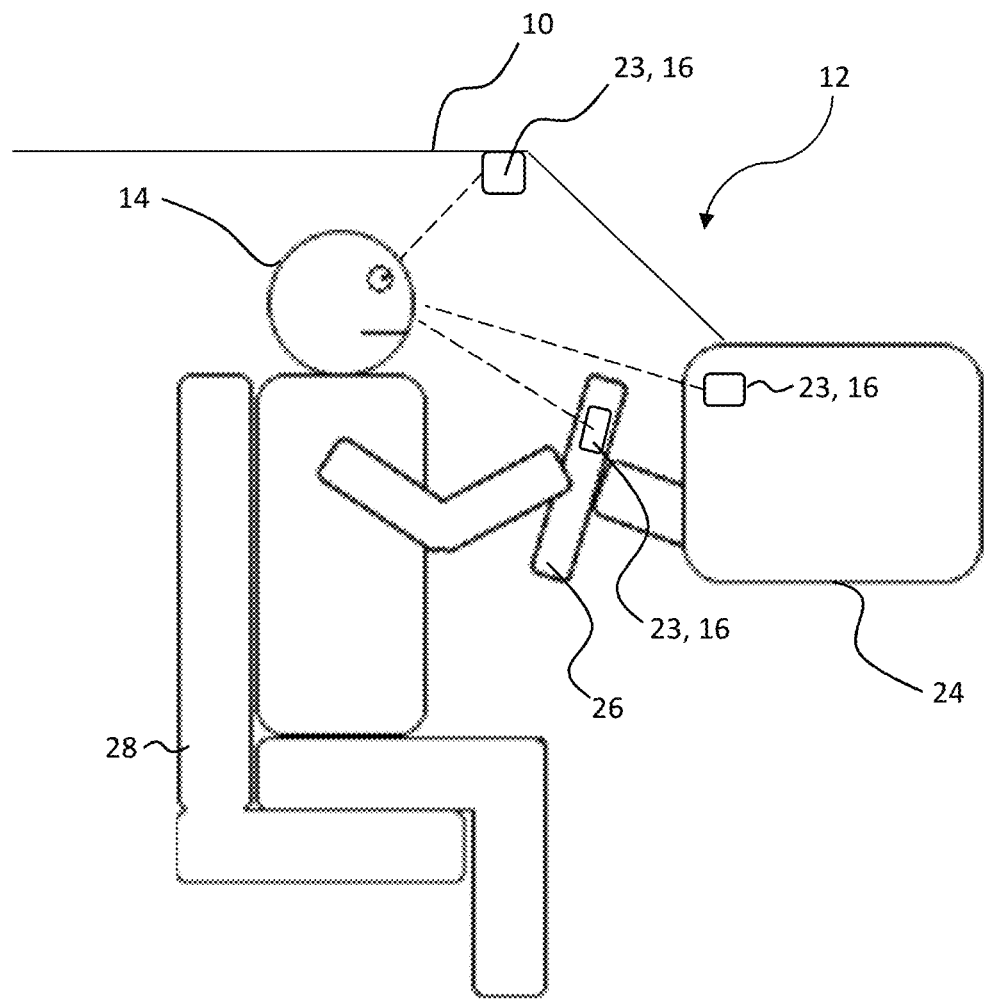
FIG. 2 is a schematic diagram illustrating an exemplary embodiment of a system for measuring passenger satisfaction.

In accordance with an exemplary embodiment, FIGS. 1-2 show a system 12 for measuring passenger satisfaction of a passenger 14 in a vehicle 10. Vehicle 10 may be an autonomous vehicle. System 12 may include a first sensor 16 and a processor 18. First sensor 16 and processor 18 may be operably connected, such as through a bus 20. First sensor 16 and processor 18 may also be operably connected via wireless communication. First sensor 16 may be structured to detect a first property of passenger 14. Exemplary embodiments of the first sensor 16 and the first property will be described in detail below. Processor 18 may be structured to calculate a passenger satisfaction index of passenger 14 based on the first property of passenger 14 detected by sensor 16.

Additionally, FIG. 1 shows that in at least an embodiment, system 12 may further include second sensor 22. Second sensor 22 may be operably coupled to processor 16, and second sensor 22 may be structured to detect a second property of passenger 14. The second property may be different than the first property. In an embodiment in which second sensor 22 is present, processor 18 may be structured to calculate the passenger satisfaction index of passenger 14 based on the first property and the second property. The first property and the second property may be objective measurements of a response of passenger 14 to operation of the autonomous vehicle, and may include biometric data of passenger 14, interpretation of gestures or words of passenger 14, or a quantification of frustration or trust of passenger 14 in the operation of autonomous vehicle 10. The first property of passenger 14 is discussed in greater detail below with illustrative examples.

The first property may include a quantification of the frustration level of passenger 14 of the operation of the autonomous operation of vehicle 10, such as a passenger frustration index $I_F$. Alternatively, the first property may include a quantification of the trust that passenger 14 has in the autonomous operation of vehicle 10, such as a passenger trust index $I_T$. The first property may also be a combination of the passenger frustration index $I_F$ and passenger trust index $I_T$.

In an exemplary embodiment, the passenger satisfaction index may be expressed by the following equation:

$$PSI = 100 - W_1(I_T) - W_2(I_F) \quad \text{(Eq. 1)}$$

PSI is the passenger satisfaction index and $W_1$, $W_2$ are weighting functions to provide scaling of passenger trust index $I_T$ and passenger frustration index $I_F$ and restrict a sum of $I_T$ and $I_F$ to 100 or less. As explained in detail below, passenger trust index $I_T$ and passenger frustration index $I_F$ can be calculated based on a variety of different types of inputs. Thus, weighting functions $W_1$ and $W_2$ can be used to normalize and weight the passenger trust index $I_T$ and passenger frustration index $I_F$ into a unitless format for easier analysis and comparison. Weighting functions $W_1$ and $W_2$ may be a constant coefficient, or may be variable functions based on the type or amount of data being considered. Alternatively, one of the weighting functions $W_1$, $W_2$ may be set to 0 if a particular value is not being used in the calculation of the passenger satisfaction index PSI.

In this exemplary embodiment, the passenger satisfaction index PSI is designed to have a baseline value of 100. However, it will be understood that this is not required, and the baseline value may be set as desired by the manufacturer. For example, a baseline value of 0 could be used instead.

Additionally, it will be understood that the calculation of the passenger satisfaction index PSI is not limited to subtraction operations as shown above. The exact operations used will depend on the definition of the passenger trust index $I_T$ and passenger frustration index $I_F$, and how these values are calculated. For example, in one embodiment, a higher value of passenger satisfaction index PSI may indicate greater level of satisfaction of passenger 14, while a lower value of passenger satisfaction index PSI may indicate a lower level of satisfaction of passenger 14. Alternatively, in another embodiment, a higher level of passenger satisfaction index PSI may indicate a lover level of satisfaction of passenger 14, while a lower value of passenger satisfaction index PSI may include a higher level of satisfaction of passenger 14. Accordingly, the sign of the operations and the sign of the values of passenger trust index $I_T$ and passenger frustration index $I_F$ will depend on the frame of reference for evaluating passenger satisfaction index PSI.

Passenger trust index $I_T$ may be based on a variety of inputs based on observation of passenger 14. For example, passenger trust index $I_T$ may be calculated based on a road monitoring duration value DMR, a secondary activity duration value DSA, a multi-task activity transaction value MAT, a side window glance value GSW, or a facial gesture value FGV. In an exemplary embodiment, passenger trust index $I_T$ may be based on the following equation:

$$I_T = W_3(\text{DMR}) + W_4(\text{DSA}) + W_5(\text{MAT}) + W_6(\text{GSW}) + W_7(\text{FGV}) \quad \text{(Eq. 2)}$$

$W_3$, $W_4$, $W_5$, $W_6$, and $W_7$ are weighting functions for scaling and normalization. Each of the road monitoring duration value DMR, the secondary activity duration value DSA, the multi-task activity transaction value MAT, the side window glance value GSW, and the facial gesture value FGV may have different ranges of possible values or different magnitudes. Accordingly, weighting functions $W_3$, $W_4$, $W_5$, $W_6$, and $W_7$ scale and normalize the values so that they can be meaningfully combined and analyzed. Weighting functions $W_3$, $W_4$, $W_5$, $W_6$, and $W_7$ may be a constant coefficient, or may be variable functions based on the type or amount of data being considered. Alternatively, one of the weighting functions $W_3$, $W_4$, $W_5$, $W_6$, and $W_7$ may be set to 0 if a particular value is not being used in the calculation of the passenger trust index $I_T$. The signs of weighting functions $W_3$, $W_4$, $W_5$, $W_6$, and $W_7$ may also be varied depending on how the specific values of the road monitoring duration value DMR, the secondary activity duration value DSA, the multi-task activity transaction value MAT, the side window glance value GSW, and the facial gesture value FGV are calculated. For example, in one embodiment, a positive value of road monitoring duration value DMR may indicate a low level of trust in the autonomous operation of vehicle 10, while a positive value of secondary activity duration value DSA may indicate a high level of trust in the autonomous operation of vehicle 10. Accordingly the signs of weighting functions $W_3$ and $W_4$ may be set opposite to each other so that the passenger trust index $I_T$ accurately reflects the meaning of the values used in the calculation.

FIG. 2 shows an exemplary embodiment of system 12 configured to calculate the road monitoring duration value DMR, the secondary activity duration value DSA, the multi-task activity transaction value MAT, the side window glance value GSW, and the facial gesture value FGV. In FIG. 2, first sensor 16 may be implemented as camera 23. Camera 23 may be provided in the dashboard 24 of vehicle 10, on an interior ceiling of vehicle 10, in a steering wheel 26, or any position where the camera can record the face of passenger 14. Lines of sight of cameras 23 are shown by dashed line in FIG. 2. While FIG. 2 shows multiple cameras 23, it will be understood that this is for illustrative purposes to show at least some possible positions of camera 23, and it will be further understood that a single camera 23 may be provided. Camera 23 may be structured to record and output a video time series of the face and head of passenger 14. Camera 23 and/or processor 18 (shown in FIG. 1) may be used to calculate a view direction of passenger 14 based on analysis of the video time series recorded by camera 23.

The road monitoring duration value DMR may be calculated based on the video time series output by camera 23 as given by the following equation:

$$DMR = \sum_{i=0}^{n} \frac{EGR(x(t))_i \Delta t}{t} \quad \text{(Eq. 3)}$$

wherein x(t) is a video time series output by the camera, EGR( ) is a function that outputs a first value if passenger 14 is glancing at the road, $\Delta t$ is a duration of the eye glance to the road, and t is a duration of the video time series.

The function EGR( ) may return a value of 1 if passenger 14 is glancing at the road and 0 otherwise. Alternatively, function EGR( ) may be designed to assign more weight (i.e., a higher value) to glances that last for a longer time. The term $\Delta t/t$ may be included as shown above in Eq. 3 as a way to weight the value by a ratio of glance period to the overall time of the video time series.

It will be understood that Eq. 3 is not the only equation possible for calculating road monitoring duration value DMR, and that the equation may be modified based on the specific needs of specific applications. Regardless of the specific equation used to calculate road monitoring duration value DMR, it will be understood that the calculation of road monitoring duration value DMR returns a value indicative of the amount of time that passenger 14 spends looking at the road. If passenger 14 spends a large percentage of time looking at the road, this could indicate a lower level of trust in the autonomous operation of vehicle 10, and the passenger trust index $I_T$ and passenger satisfaction index PSI can be adjusted accordingly. Alternatively, if the passenger is not looking at the road (e.g., looking at a phone, a book, or other passengers), this could indicate a higher level of trust in the autonomous operation of vehicle 10, and the passenger trust index $I_T$ and passenger satisfaction index PSI can be adjusted accordingly.

The secondary activity duration value DSA may be calculated based on the video time series output by camera 23 as given by the following equation:

$$DSA = \sum_{i=0}^{n} \frac{EGPD(x(t))_i \Delta t}{t} \quad \text{(Eq. 4)}$$

wherein x(t) is a video time series output by the camera, EGPD( ) is a function that outputs a first value if passenger 14 performs a secondary activity, $\Delta t$ is a duration of performing the secondary activity, and t is a duration of the video time series.

The function EGPD( ) may return a value of 1 if passenger 14 is performing a secondary activity such as using a phone, reading, looking at other passengers, or the like. Alternatively, function EGPD( ) may be designed to assign more weight (i.e., a higher value) to secondary activities that last for a longer time. The term $\Delta t/t$ may be included as shown above in Eq. 4 as a way to weight the value by a ratio of secondary activity time to the overall time of the video time series.

It will be understood that Eq. 4 is not the only equation possible for calculating secondary activity duration value DSA, and that the equation may be modified based on the specific needs of specific applications. Regardless of the specific equation used to calculate secondary activity duration value DSA, it will be understood that the calculation of secondary activity duration value DSA returns a value indicative of the amount of time that passenger 14 spends doing activities unrelated to the operation of vehicle 10. If passenger 14 spends a large percentage of time on secondary activities, this could indicate a higher level of trust in the autonomous operation of vehicle 10, and the passenger trust index $I_T$ and passenger satisfaction index PSI can be adjusted accordingly. Alternatively, if the passenger does not spend much time on secondary activities, this could indicate a lower level of trust in the autonomous operation of vehicle 10, and the passenger trust index $I_T$ and passenger satisfaction index PSI can be adjusted accordingly.

The secondary side window glance value GSW may be calculated based on the video time series output by camera 23 as given by the following equation:

$$GSW = \Sigma_{i=0}^{n}(EGSW(x(t))_i) \quad \text{(Eq. 5)}$$

wherein x(t) is a video time series output by the camera, and EGSW( ) is a function that outputs a first value if the passenger is glancing to side windows.

The function EGSW( ) may return a value of 1 if passenger 14 glances out a side window of vehicle 10. Alternatively, function EGSW( ) may be designed to assign more weight (i.e., a higher value) to longer glances or more frequent glances out the side window.

It will be understood that Eq. 5 is not the only equation possible for calculating side window glance value GSW, and that the equation may be modified based on the specific needs of specific applications. Regardless of the specific equation used to calculate side window glance value GSW, it will be understood that the calculation of side window glance value GSW returns a value indicative the number of times or the amount of time that passenger 14 spends looking out the side window of vehicle 10. If passenger 14 spends a large percentage of time looking out the side window, this could indicate a higher level of trust in the autonomous operation of vehicle 10, and the passenger trust index $I_T$ and passenger satisfaction index PSI can be adjusted accordingly. Alternatively, if passenger 14 does not look out the side window very often, this could indicate a lower level of trust in the autonomous operation of vehicle 10 and the passenger trust index $I_T$ and passenger satisfaction index PSI can be adjusted accordingly.

The multi-task activity transaction value MAT may be calculated based on the video time series output by camera 23 as given by the following equation:

$$\text{MAT} = \Sigma_{i=0}^{n}(\text{EGR}(x(t))_i + \text{EGPD}(x(t))_i + \text{EGVD}(x(t))_i + \text{EGSW}(x(t))_i) \quad \text{(Eq. 6)}$$

wherein x(t) is a video time series output by the camera, EGR( ) is a function that outputs a first value if passenger 14 is glancing at the road, EGPD( ) is a function that outputs a second value if passenger 14 is performing a secondary activity; EGVD( ) is a function that outputs a third value if passenger 14 is glancing at vehicular devices; and EGSW( ) is a function that outputs a fourth value if passenger 14 is glancing to side windows.

Functions EGR( ), EGPD( ), and EGSW( ), are described in detail above. Function EGVD( ) may return a value of 1 if passenger 14 glances at vehicular devices such as controls, gauges, or displays. Alternatively EGVD( ) may be designed to adjust the value depending on the length of the glance at the vehicular device.

It will be understood that Eq. 6 is not the only equation possible for multi-task activity transaction value MAT, and that the equation may be modified based on the specific needs of specific applications. Regardless of the specific equation used to calculate multi-task activity transaction value MAT, it will be understood the calculation of multi-task activity transaction value MAT returns a value indicative of a level of multi-tasking by passenger 14. If passenger 14 spends a large amount of time multi-tasking, this could indicate a higher level of trust in the autonomous operation of vehicle 10, and the passenger trust index $I_T$ and passenger satisfaction index PSI can be adjusted accordingly. Alternatively, if passenger 14 does not spend much time multitasking, this could indicate a lower level of trust in the autonomous operation of vehicle 10, and the passenger trust index $I_T$ and passenger satisfaction index PSI can be adjusted accordingly. Even if the passenger 14 does not spend much time multi-tasking, the calculation of multi-task activity transaction value MAT could be modified to still reflect a high level of trust in autonomous operation of vehicle 10 if the majority of attention of passenger 14 is focused on secondary activities or looking out the side windows, for example.

The facial gesture value FGV may be calculated based on the video time series output by camera 23 as given by the following equation:

$$\text{FGV} = \Sigma_{i=0}^{n}(FAC(x(t))_i) \quad \text{(Eq. 7)}$$

wherein x(t) is the video time series output by the camera, FAC( ) is a facial expression of passenger 14; and V( ) is a function that outputs a first value if the facial expression is one of a first group of facial expressions, and outputs a second value if the facial expression is one of a second group of facial expressions.

Camera 23 and processor 18 (shown in FIG. 1) may be structured to interpret a face of passenger 14 and classify a facial expression of passenger 14 into one of two groups. This classification can be based on recognizing patterns in the shape and structure of eyebrows, eyes, mouth, and other relevant features of the face of passenger 14. For example, the first group may include positive facial expressions such as surprise, happiness, interest, or calm. The second group may include negative facial expressions such as sadness, fear, anger, disgust, contempt, horror, discomfort, or stoicism. If the function FAC( ) determines that a facial gesture of passenger 14 is in the first group, the function V( ) could increment the facial gesture value FGV by 1. Alternatively, if the function FAC( ) determines that a facial gesture of passenger 14 is in the second group, the function V( ) could decrement the facial gesture value FGV by 1. In this way, facial gesture value FGV could be a net measure of the trust of passenger 14 in the operation of autonomous vehicle 10. In other words, a facial gesture value FGV indicating more positive facial gestures could indicate a higher level of trust in the autonomous operation of vehicle 10, and the passenger trust index $I_T$ and passenger satisfaction index PSI can be adjusted accordingly. Alternatively, a facial gesture value FGV indicating more negative facial gestures could indicate a lower level of trust in the autonomous operation of vehicle 10, and the passenger trust index $I_T$ and passenger satisfaction index PSI can be adjusted accordingly.

Passenger frustration index $I_F$ may be based on a variety of inputs based on observation of passenger 14. For example, passenger frustration index $I_F$ may be calculated based on a galvanic skin response value GSR, a skin temperature value ST, a verbal valence value VV, or a facial gesture value FGV. In an exemplary embodiment, passenger frustration index $I_F$ may be based on the following equation:

$$I_F = W_8(\text{GSR}) + W_9(\text{ST}) W_{10}(\text{VV}) + W_{11}(\text{FGV}) \quad \text{(Eq. 8)}$$

$W_8$, $W_9$, $W_{10}$, and $W_{11}$ are weighting functions for scaling and normalization. Each of the galvanic skin response value GSR, the skin temperature value ST, the verbal valence value VV, and the facial gesture value FGV may have different ranges of possible values or different magnitudes. Accordingly, weighting functions $W_8$, $W_9$, $W_{10}$, and $W_{11}$ scale and normalize the values so that they can be meaningfully combined and analyzed. Weighting functions $W_8$, $W_9$, $W_{10}$, and $W_{11}$ may be a constant coefficient, or may be variable functions based on the type or amount of data being considered. Alternatively, one of the weighting functions $W_8$, $W_9$, $W_{10}$, and $W_{11}$ may be set to 0 if a particular value is not being used in the calculation of the passenger frustration index $I_T$. Additionally, the signs of weighting functions $W_8$, $W_9$, $W_{10}$, and $W_{11}$ may also be varied depending on how the specific values of the galvanic skin response value GSR, the skin temperature value ST, the verbal valence value VV, and the facial gesture value FGV are calculated. For example, in one embodiment, a positive value of galvanic skin response value GSR may indicate a high level of frustration with the autonomous operation of vehicle 10, while a positive value of facial gesture value FGV may indicate a low level of frustration with the autonomous operation of vehicle 10. Accordingly, the signs of weighting functions $W_8$ and $W_{11}$ may be set opposite to each other so that the passenger frustration index $I_F$ accurately reflects the meaning of the values used in the calculation.

Figure 3:
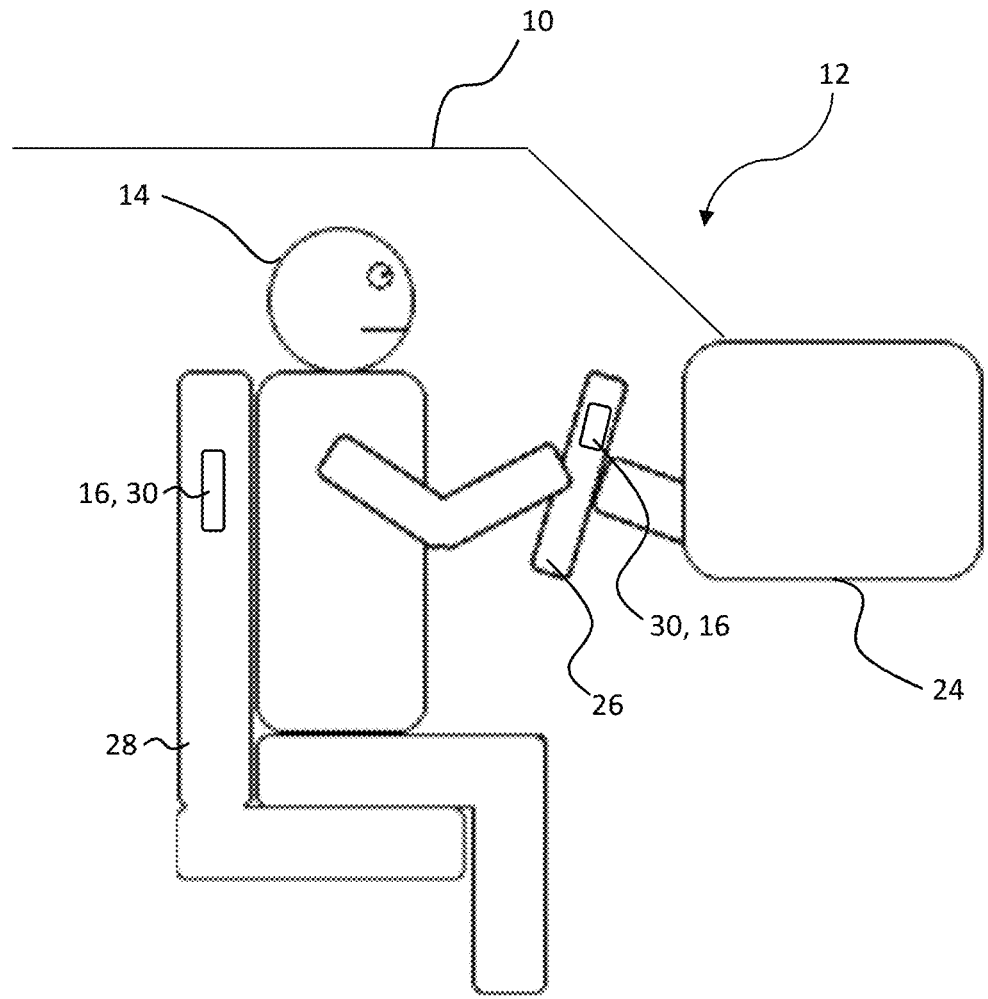
FIG. 3 is a schematic diagram illustrating an exemplary embodiment of a system for measuring passenger satisfaction.

FIG. 3 shows an exemplary embodiment of system 12 configured to calculate the galvanic skin response value GSR or the skin temperature value ST. In FIG. 3, first sensor 16 may be implemented as a skin sensor 30. Skin sensor 30 may be provided in steering wheel 26, and may be structured to detect electrical properties of skin of passenger 14 (e.g., resistance, voltage, current, capacitance, etc.) or detect a skin temperature of passenger 14. Alternatively, it may be possible to provide a skin sensor 30 within seat 28 if calibrated properly to account for clothing and set material between the skin sensor 30 and the skin of passenger 14. While FIG. 3 shows multiple skin sensors 30, it will be understood that this is for illustrative purposes to show at least some possible positions of skin sensor 30, and it will be further understood that a single skin sensor 30 may be provided. Skin sensor 30 is structured to output a signal corresponding to the electrical properties of the skin of passenger 14 or the temperature of the skin of passenger 14, and the signal can be analyzed and processed by processor 18 (see FIG. 1).

The galvanic skin response value may be calculated based on the signal from skin sensor 30 configured to detect electrical properties as given by the following equation:

$$GSR = \Sigma_{i=0}^{n} F(x(t))_i \qquad (Eq. 9)$$

wherein x(t) is a signal time series of the signal output by skin sensor 30; and F( ) is a function that outputs a first value if a signal level satisfies a first predetermined criteria.

For example, the function F( ) may increment the galvanic skin response by a set value if electrical properties of the skin of passenger 14 exceed or are lower than a specified threshold. Alternatively, function F( ) may increment the galvanic skin response GSR by a set value if electrical properties of the skin of passenger 14 change by a specified amount or for a specified duration of time.

It will be understood that Eq. 9 is not the only equation possible for calculating galvanic skin response GSR, and that the equation may be modified based on the specific needs of specific applications. Regardless of the specific equation used to calculate galvanic skin response value GSR, it will be understood that the calculation of galvanic skin direction value GSR returns a value indicative of an electrical response of passenger 14. High levels of electrical response or rapid or large changes in electrical response of passenger 14 could indicate a higher level of frustration with the autonomous operation of vehicle 10, and the passenger frustration index $I_F$ and passenger satisfaction index PSI could be adjusted accordingly. Alternatively, low levels of electrical response or a relatively constant level of electrical response of passenger 14 could indicate a lower level of frustration with the autonomous operation of vehicle 10, and the passenger frustration index $I_F$ and passenger satisfaction index PSI could be adjusted accordingly.

The skin temperature value ST may be calculated based on signals from a skin sensor 30 configured to detect temperature. Alternatively, skin temperature value ST may be calculated from images captured by camera 23 (see FIG. 2) if camera 23 includes infrared elements structured to detect temperature. Skin temperature value ST may be given by the following equation:

$$ST = \Sigma_{i=0}^{n} F(x(t))_i \qquad (Eq. 10)$$

wherein x(t) is a signal time series of the signal output by skin sensor 30 or camera 23; and F( ) is a function that outputs a first value if a signal level satisfies a first predetermined criteria.

For example, function F( ) may increment the skin temperature value ST by a set value if the skin temperature of passenger 14 exceeds or is lower than a specified threshold. Alternatively, function F( ) may increment the skin temperature value ST by a set value if the skin temperature of passenger 14 changes by a specified amount or for a specified duration of time.

It will be understood that Eq. 10 is not the only equation possible for calculating skin temperature response ST, and that the equation may be modified based on the specific needs of specific applications. Regardless of the specific equation used to calculate skin temperature response ST, it will be understood that the calculation of skin temperature response ST returns a value indicative the skin temperature of passenger 14. High levels of skin temperature or rapid or large changes in skin temperature of passenger 14 could indicate a higher level of frustration with the autonomous operation of vehicle 10, and the passenger frustration index $I_F$ and passenger satisfaction index PSI could be adjusted accordingly. Alternatively, low levels of skin temperature or relatively constant level of skin temperature could indicate a lower level of frustration with the autonomous operation of vehicle 10, and the passenger frustration index $I_F$ and passenger satisfaction index PSI could be adjusted accordingly.

Figure 4:
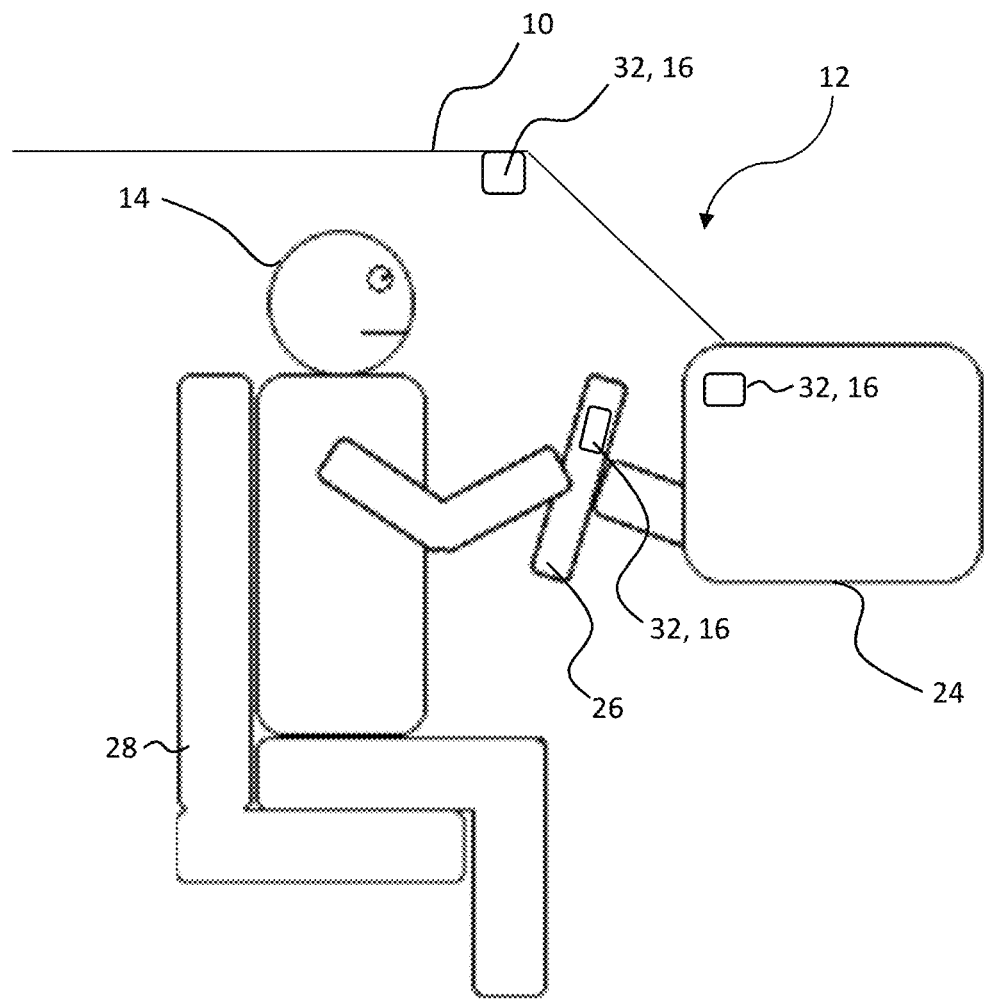
FIG. 4 is a schematic diagram illustrating an exemplary embodiment of a system for measuring passenger satisfaction.

FIG. 4 shows an exemplary embodiment of system 12 configured to calculate verbal valence value VV. In FIG. 3 first sensor 16 may be implemented as a microphone 32. Microphone 32 may be provided in dashboard 24, provided in steering wheel 26, provided on an interior ceiling of vehicle 10, or any other suitable position where the voice of passenger 14 can be detected. While FIG. 4 shows multiple microphones 32, it will be understood this this is for illustrative purposes to show at least some possible positions of microphone 32, and it will be further understood that a single microphone 32 may be provided. Microphone 32 may be structured to record and output a sound time series of an audio environment inside vehicle 10.

The verbal valence value may be calculated based on the sound time series recorded by microphone 32 as given by the following equation:

$$VV = \Sigma_{i=0}^{n} S(\text{Verbal}(x(t)))_i \qquad (Eq. 11)$$

wherein x(t) is a sound time series of the output of microphone 32; Verbal( ) is function identifying a word spoken by passenger 14; and S( ) is a function that outputs a first value if the word spoken by passenger 14 is one of a first group of words, and outputs a second value if the word spoken by passenger 14 is one of a second group of words.

Microphone 32 and processor 18 (see FIG. 1) may be structured to identify and interpret a word or phrase spoken by passenger 14. It will be understood that in the description below, references to a word spoken by passenger 14 will also include a phrase spoken by passenger 14. The word spoken by passenger 14 can be classified into one of two groups. For example, the first group may include positive words such as "nice," "good," "best," "comfortable," "better," "great,"

"more," "smooth," "fantastic," "safe," etc. The second group may include negative words such as "than I would," "would have," "not," "concerned," "whew," "uncomfortable," "nervous," "don't," "terrible," "didn't," "reckless," "unsafe," "less," "dangerous," "extreme," "wow," etc. If function Verbal( ) determines that a word is in the first group, the function S( ) could increment the verbal valence value VV by 1. Alternatively, if the function Verbal( ) determines that a word is in the second group, the function V( ) could decrement the verbal valence value VV by 1. In this way, verbal valence value could be a net measure of the frustration of user 14 with the autonomous operation of vehicle 10 based on the spoken utterances of passenger 14. In other words, a verbal valence value VV indicating more positive words could indicate a lower level of frustration with the autonomous operation of vehicle 10, and the passenger frustration index $I_F$ and passenger satisfaction index PSI can be adjusted accordingly. Alternatively, a verbal valence value indicating more negative words could indicate a higher level of frustration with the autonomous operation of vehicle 10, and the passenger frustration index $I_F$ and passenger satisfaction index PSI can be adjusted accordingly.

With respect to passenger frustration index $I_F$, the facial gesture value FGV may be calculated in similar fashion as described above with respect to the passenger trust index $I_T$.

Figure 5:
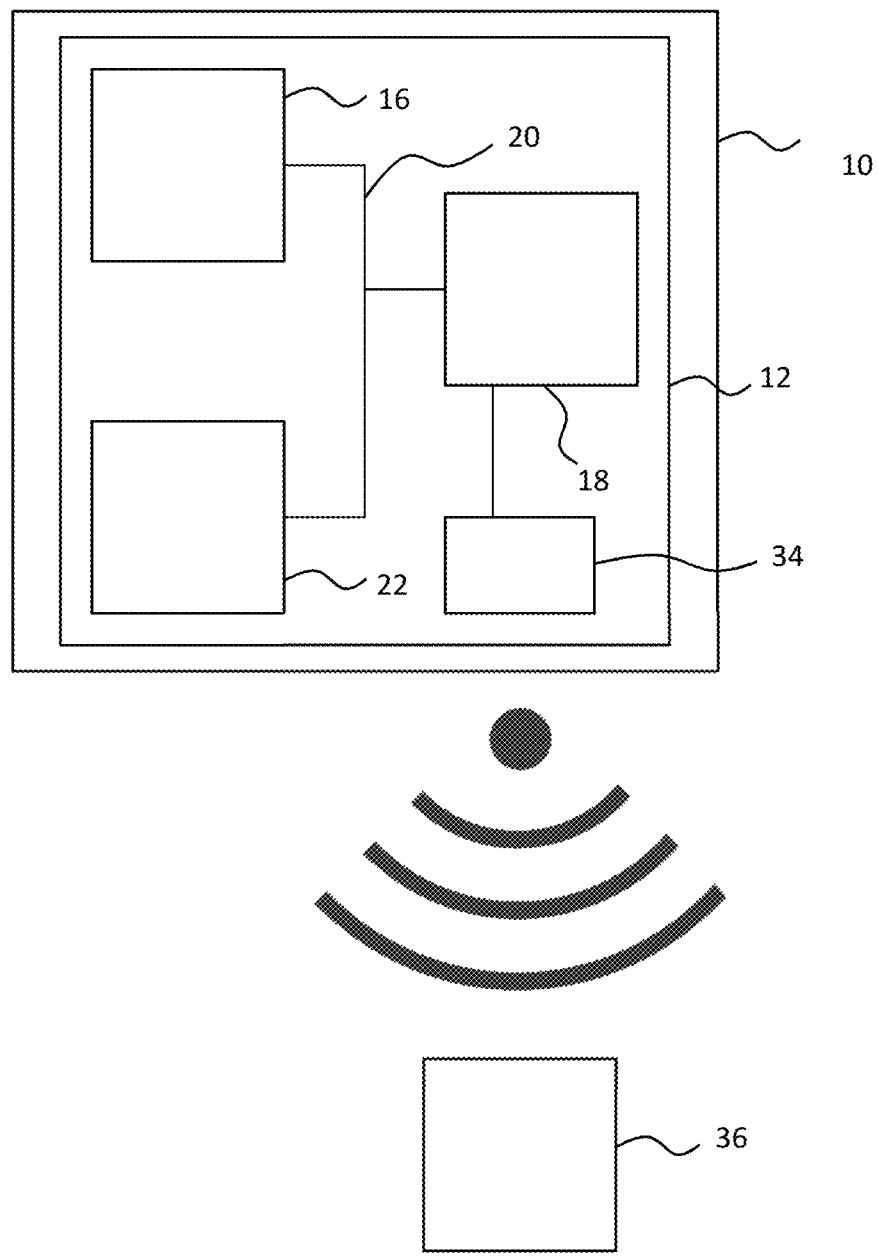
FIG. 5 is a schematic diagram illustrating an exemplary embodiment of a system for measuring passenger satisfaction.

FIG. 5 shows an exemplary embodiment in which system 12 includes a communication node 34 structured to communicate with an external device 36. Communication node 34 may be operably connected to processor 18 so that processor 18 can receive and operate on data received via communication node 34. Communication node 34 may be any type of transmitter/receiver capable of wireless communication. For example, communication node 34 may be a WI-FI transmitter/receiver, a Bluetooth transmitter receiver, an RF transmitter/receiver, a cellular transmitter/receiver, or other suitable type of device.

Figure 6:
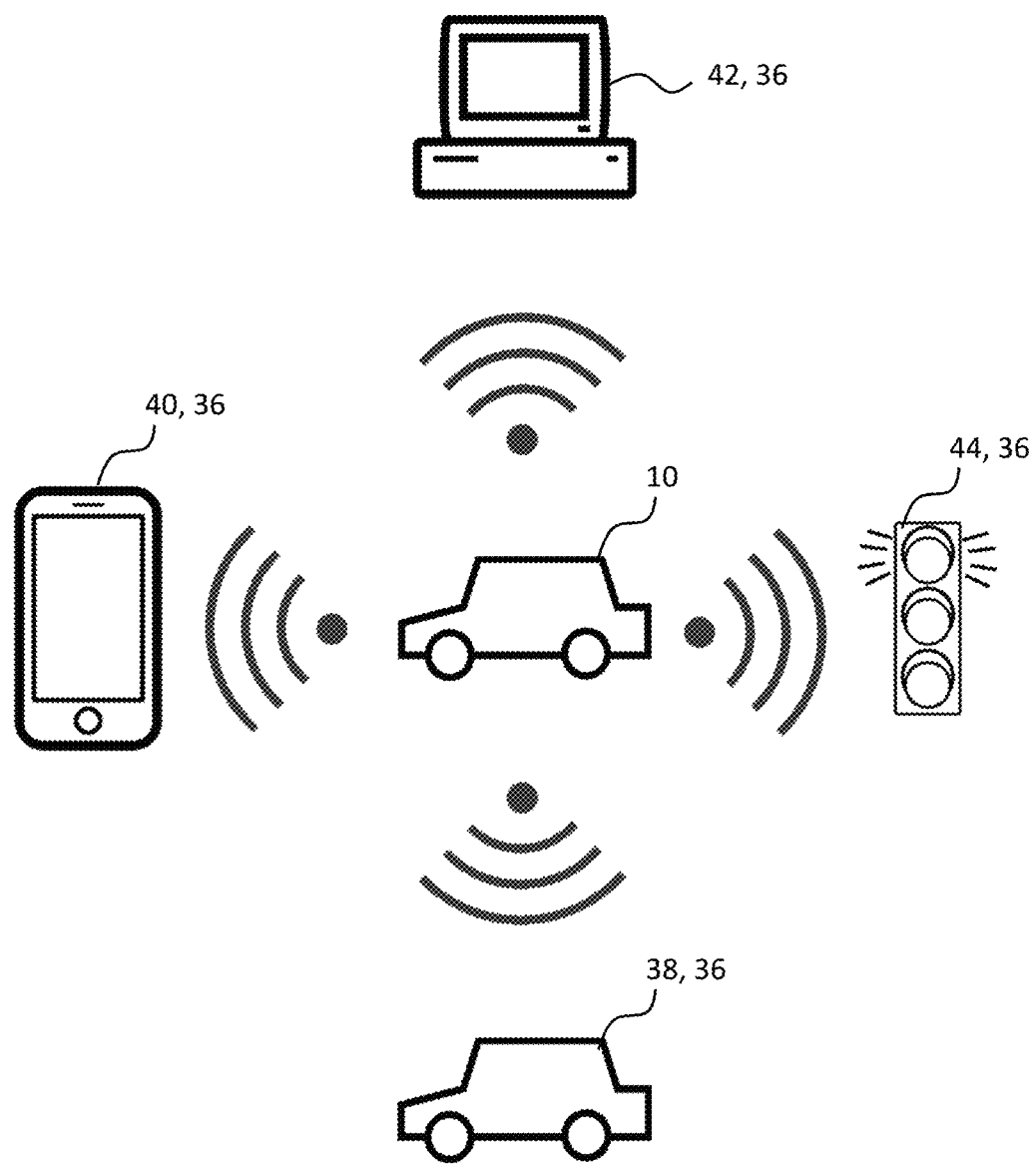
FIG. 6 is a schematic diagram illustrating an exemplary embodiment of a system for measuring passenger satisfaction.

External device 36 may be any type of device capable of wireless communication with communication node 34. FIG. 6 shows exemplary embodiments of possible external devices that vehicle 10 could communicate with via communication node 34 (see FIG. 3). For example, external device 36 may be another vehicle 38 equipped with a communication node, a smartphone 40, a computer 42 accessible via the internet, or smart infrastructure objects such as stoplight 44.

In these embodiments, processor 18 could receive information such as local traffic data, local weather data, passenger social data, passenger calendar data, or destination data from an external device 36. This information could be used by processor 18 to modify the passenger satisfaction index PSI. For example, if there is heavy traffic or bad weather, processor 18 could modify the passenger satisfaction index PSI to reflect that passenger 14 may be feeling additional nervousness in these situations. Alternatively, with access to social data, calendar data, or destination, processor 18 could modify the passenger satisfaction index to reflect where the passenger is headed (e.g., happier for social gathering, more nervous for a client meeting, etc.), and processor 18 could also modify the autonomous operation of vehicle 18 to account for important events, such as making it to an airport in time for a flight. For example, passenger 14 may exhibit objective criteria indicating a high level of frustration, i.e., a high passenger frustration index $I_F$, but if processor 18 is aware that passenger is possibly late for an appointment or a flight, this could be taken into account and autonomous operation of vehicle 10 could be adjusted accordingly. Adjusting autonomous operation of vehicle 10 will be described in greater detail below.

Figure 7:
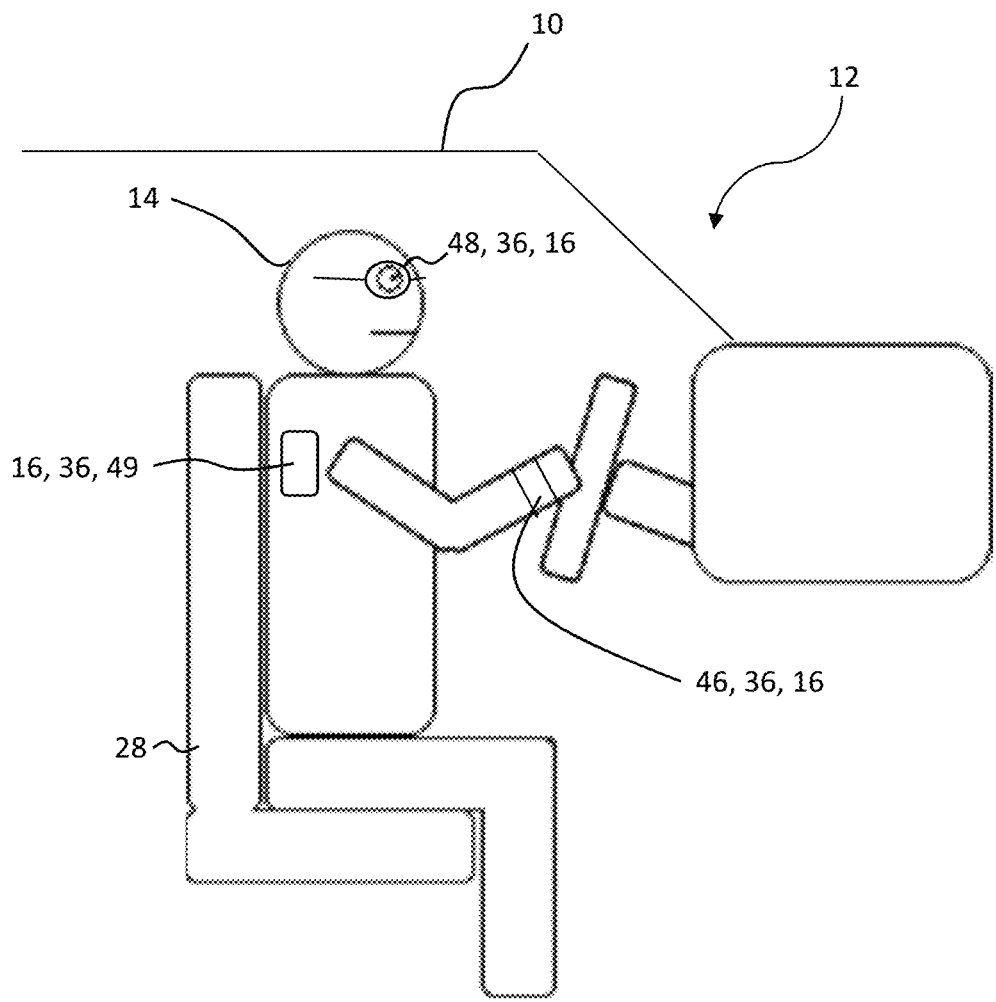
FIG. 7 is a schematic diagram illustrating an exemplary embodiment of a system for measuring passenger satisfaction.

FIG. 7 shows additional exemplary embodiments of external device 36 implemented as wearable smart devices worn by passenger 14. For example, external device 36 may be a smart watch 46, smart glasses 48, or a biometric sensor 49 worn by the passenger such as a heart monitor, blood pressure monitor, glucose monitor, etc. It will be understood that these wearable smart devices could also serve as first sensor 16 (see FIG. 1) and transmit information such as electrical properties of skin, skin temperature, or heart rate to processor 18 via communication node 34 to aid in calculation of passenger frustration index $I_F$ or passenger trust index $I_T$.

Figure 8:
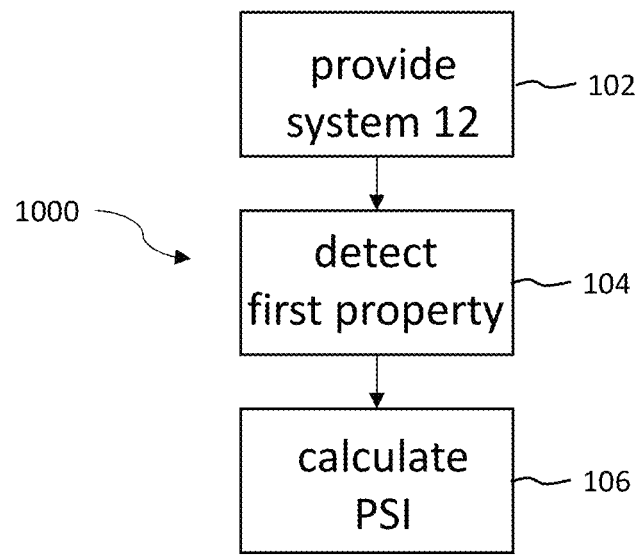
FIG. 8 is a flowchart diagram of an exemplary embodiment of a method for measuring passenger satisfaction.

FIG. 8 shows an exemplary embodiment of a method 1000 for measuring passenger satisfaction of passenger 14. In block 102, a system 12 is provided including first sensor 16 and processor 18. System 12, first sensor 16, and processor 18 are described in detail herein. In block 104, first sensor 16 is used to detect a first property of passenger 14. In block 106, processor 18 calculates passenger satisfaction index PSI based on the first property received from first sensor 16. Exemplary embodiments of detecting a first property of passenger 14 and calculating passenger satisfaction index PSI are described herein.

Figure 9:
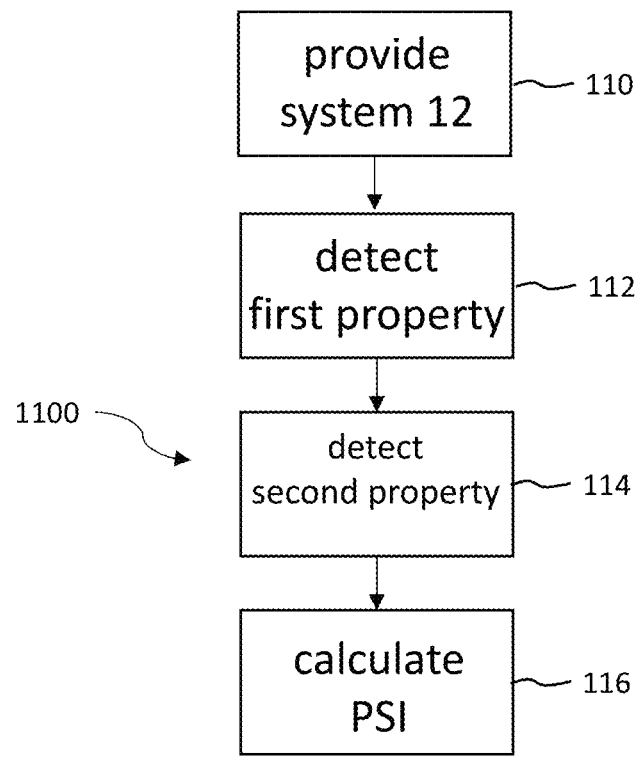
FIG. 9 is a flowchart diagram of an exemplary embodiment of a method for measuring passenger satisfaction.

FIG. 9 shows an exemplary embodiment of a method 1100 for measuring passenger satisfaction of passenger 14. In block 110, a system 12 (see FIG. 1) is provided including first sensor 16, processor 18, and second sensor 22. In block 112, first sensor 16 is used to detect a first property of passenger 14. In block 114, second sensor 14 is used to detect a second property of passenger 14. In block 116, processor 18 calculates passenger satisfaction PSI based on the first property received from first sensor 16 and the second property received from second sensor 18.

Figure 10:
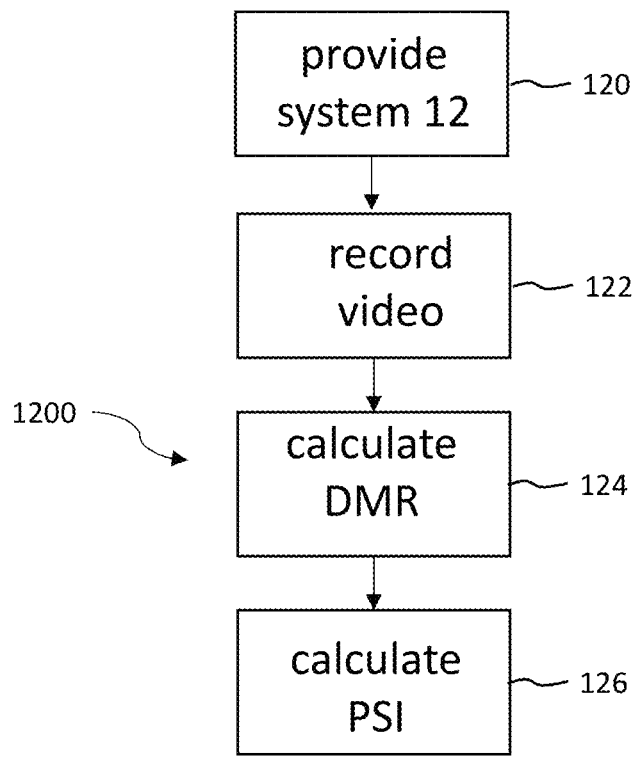
FIG. 10 is a flowchart diagram of an exemplary embodiment of a method for measuring passenger satisfaction.

FIG. 10 shows an exemplary embodiment of a method 1200 for measuring passenger satisfaction of passenger 14. In block 120, a system 12 (see FIGS. 1-2) is provided including processor 18 and camera 23. In block 122, camera 23 is used to record a video time series. In block 124, processor 18 calculates a road monitoring duration value DMR based on the video time series, as described in detail above. In block 126, processor 18 calculates passenger satisfaction index PSI based on road monitoring duration value DMR.

Figure 11:
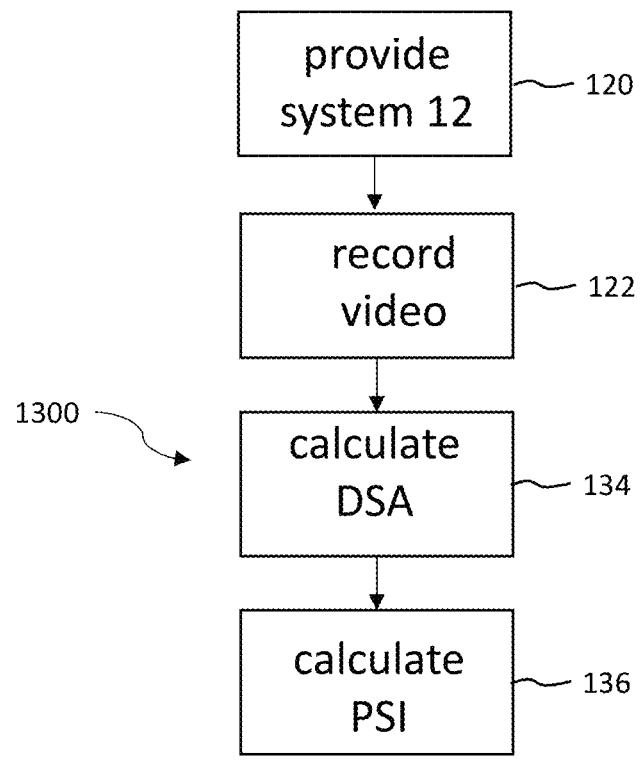
FIG. 11 is a flowchart diagram of an exemplary embodiment of a method for measuring passenger satisfaction.

FIG. 11 shows an exemplary embodiment of a method 1300 for measuring passenger satisfaction of passenger 14. In block 120, a system 12 (see FIGS. 1-2) is provided including processor 18 and camera 23. In block 122, camera 23 is used to record a video time series. In block 134, processor 18 calculates a secondary activity duration value DSA based on the video time series, as described in detail above. In block 136, processor 18 calculates passenger satisfaction index PSI based on secondary activity duration value DSA.

Figure 12:
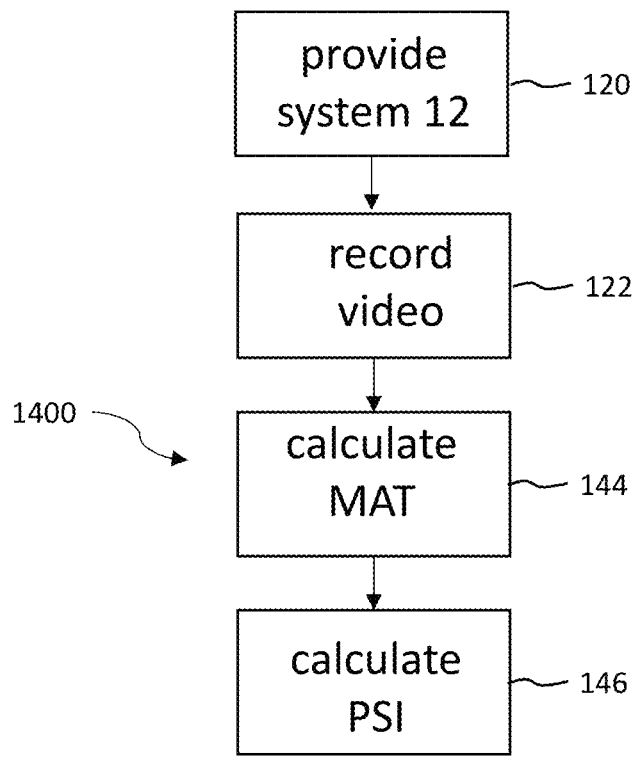
FIG. 12 is a flowchart diagram of an exemplary embodiment of a method for measuring passenger satisfaction.

FIG. 12 shows an exemplary embodiment of a method 1400 for measuring passenger satisfaction of passenger 14. In block 120, a system 12 (see FIGS. 1-2) is provided including processor 18 and camera 23. In block 122, camera 23 is used to record a video time series. In block 144, processor 18 calculates a multi-task activity transaction value MAT based on the video time series, as described in detail above. In block 146, processor 18 calculates passenger satisfaction index PSI based on multi-task activity transaction value MAT.

Figure 13:
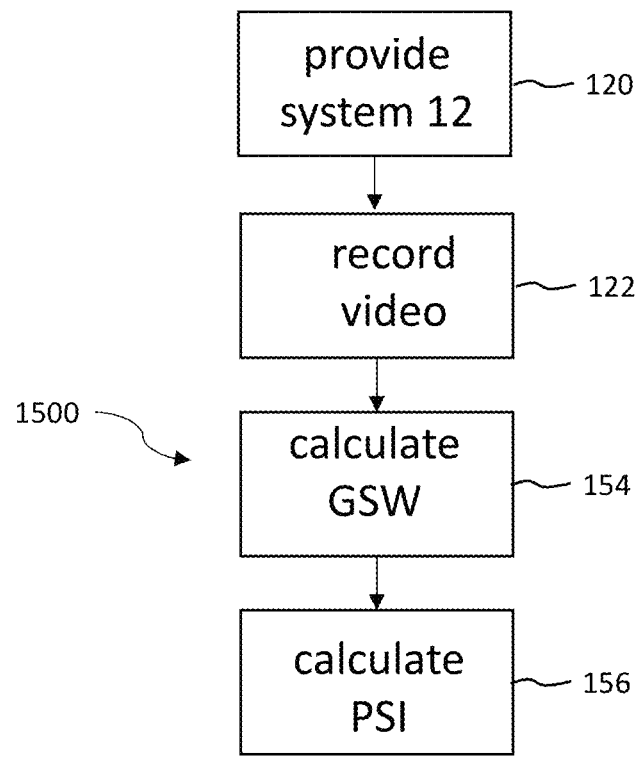
FIG. 13 is a flowchart diagram of an exemplary embodiment of a method for measuring passenger satisfaction.

FIG. 13 shows an exemplary embodiment of a method 1500 for measuring passenger satisfaction of passenger 14.

In block 120, a system 12 (see FIGS. 1-2) is provided including processor 18 and camera 23. In block 122, camera 23 is used to record a video time series. In block 154, processor 18 calculates a side window glance value GSW based on the video time series, as described in detail above. In block 156, processor 18 calculates passenger satisfaction index PSI based on side window glance value GSW.

Figure 14:
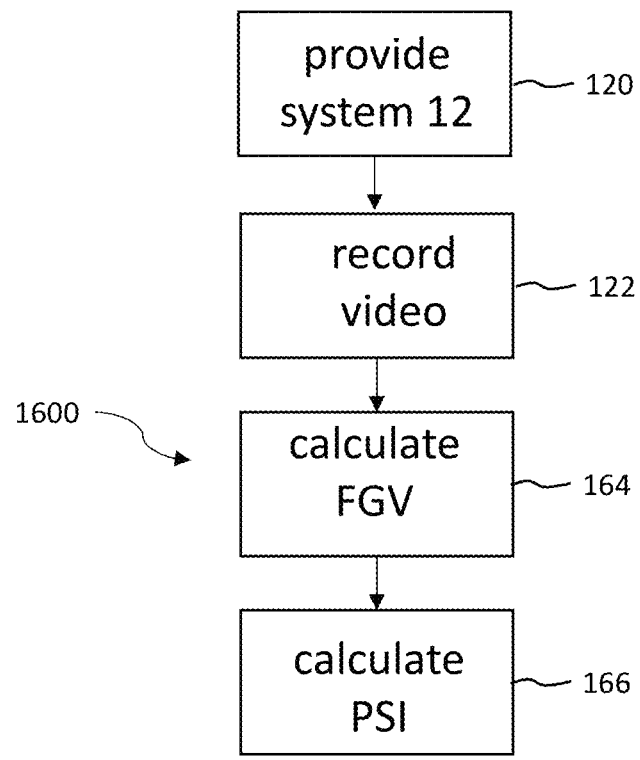
FIG. 14 is a flowchart diagram of an exemplary embodiment of a method for measuring passenger satisfaction.

FIG. 14 shows an exemplary embodiment of a method 1600 for measuring passenger satisfaction of passenger 14. In block 120, a system 12 (see FIGS. 1-2) is provided including processor 18 and camera 23. In block 122, camera 23 is used to record a video time series. In block 164, processor 18 calculates a facial gesture value FGV based on the video time series, as described in detail above. In block 166, processor 18 calculates passenger satisfaction index PSI based on facial gesture value FGV.

Figure 15:
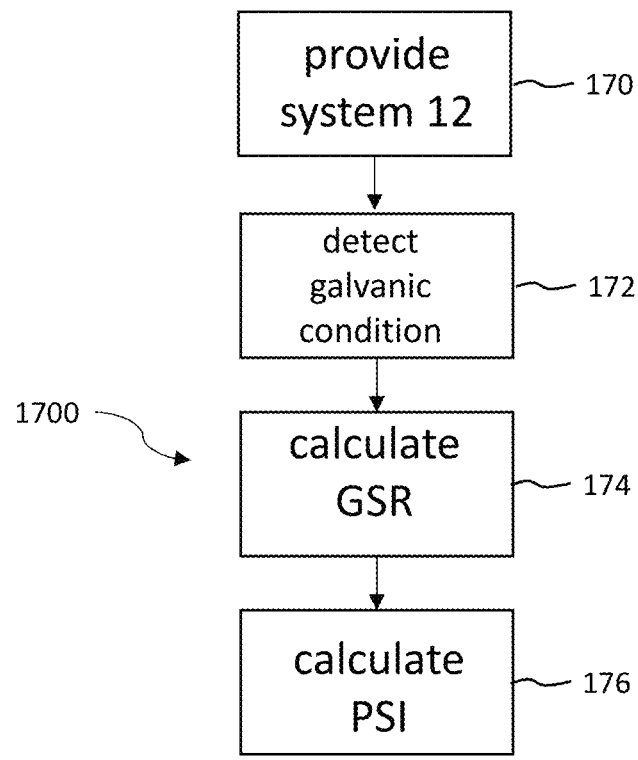
FIG. 15 is a flowchart diagram of an exemplary embodiment of a method for measuring passenger satisfaction.

FIG. 15 shows an exemplary embodiment of a method 1700 for measuring passenger satisfaction of passenger 14. In block 170, a system 12 (see FIGS. 1 and 3) is provided including processor 18 and skin sensor 30. In block 172, skin sensor 30 is used to detect a galvanic condition of the skin of passenger 14. In block 174, processor 18 calculates galvanic skin response value GSR based on the galvanic condition detected by skin sensor 30, as described in detail above. In block 176, processor 18 calculates passenger satisfaction index PSI based on galvanic skin response value GSR.

Figure 16:
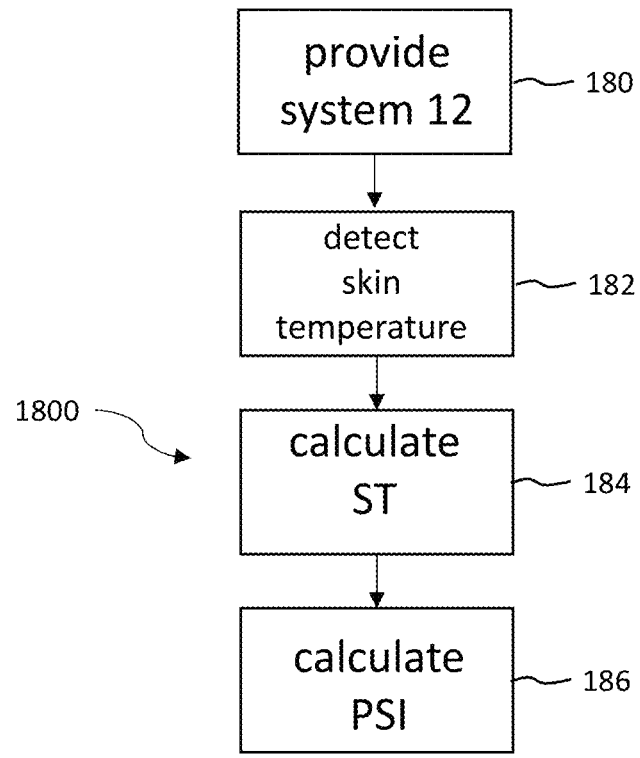
FIG. 16 is a flowchart diagram of an exemplary embodiment of a method for measuring passenger satisfaction.

FIG. 16 shows an exemplary embodiment of a method 1800 for measuring passenger satisfaction of passenger 14. In block 180, a system 12 (see FIGS. 1 and 3) is provided including processor 18 and skin sensor 30. In block 182, skin sensor 30 is used to detect a skin temperature of passenger 14. In block 184, processor 18 calculates skin temperature value ST based on the skin temperature detected by skin sensor 30, as described in detail above. In block 186, processor 18 calculates passenger satisfaction index PSI based on skin temperature value ST.

Figure 17:
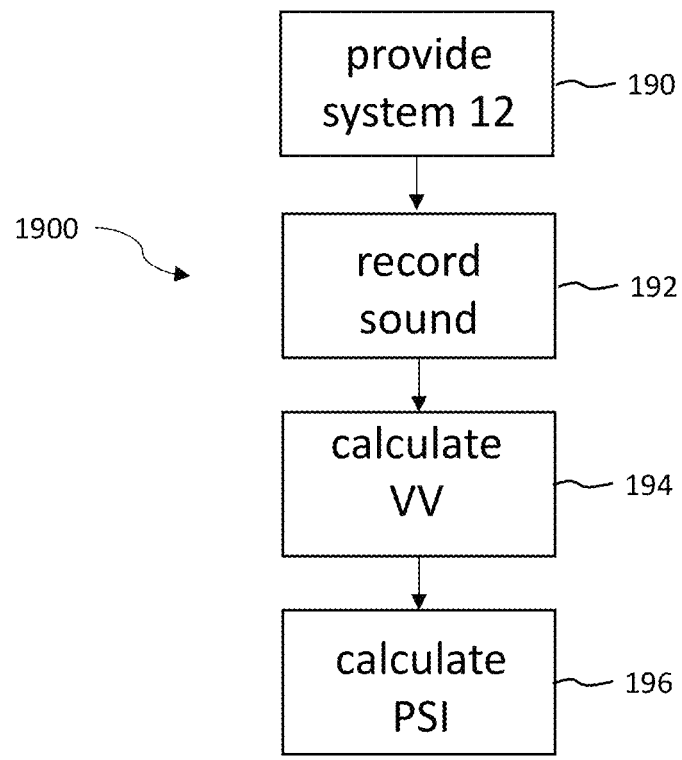
FIG. 17 is a flowchart diagram of an exemplary embodiment of a method for measuring passenger satisfaction.

FIG. 17 shows an exemplary embodiment of a method 1900 for measuring passenger satisfaction of passenger 14. In block 190, a system 12 (see FIGS. 1 and 4) is provided including processor 18 and microphone 32. In block 192, microphone 32 is used to record a sound time series. In block 194, processor 18 calculates verbal valence value VV based on the sound time series recorded by microphone 32, as described in detail above. In block 196, processor 18 calculates passenger satisfaction index PSI based on verbal valence value VV.

Figure 18:
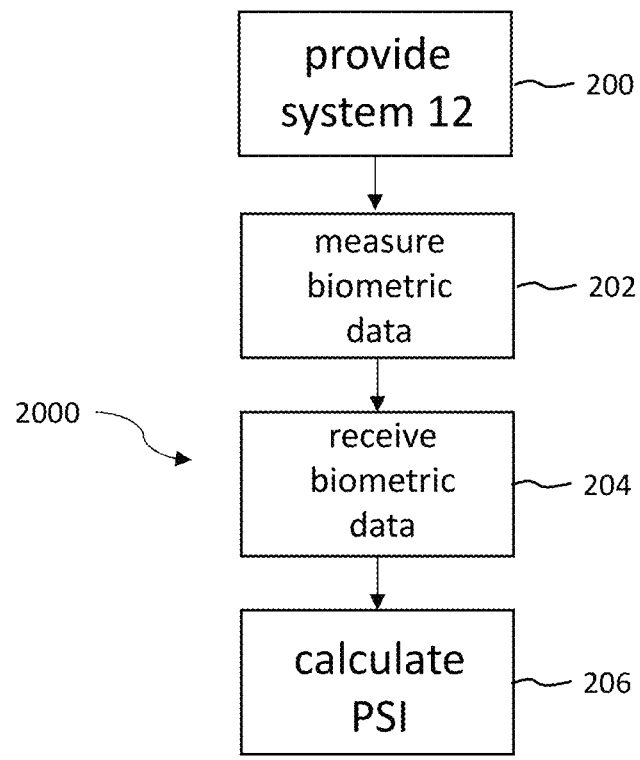
FIG. 18 is a flowchart diagram of an exemplary embodiment of a method for measuring passenger satisfaction.

FIG. 18 shows an exemplary embodiment of a method 2000 for measuring passenger satisfaction of passenger 14. In block 200, a system 12 (see FIGS. 5-7) is provided including processor 18, a communication node 34, and a wearable smart device as first sensor 16. In block 202, the wearable smart device is used to measure biometric data of passenger 14 such as galvanic skin response, skin temperature or heart rate. In block 204, processor 18 receives the biometric data from the wearable smart device via communication node 34. In block 206, processor 18 calculates the passenger satisfaction index PSI based on the biometric data received from the wearable smart devices.

Figure 19:
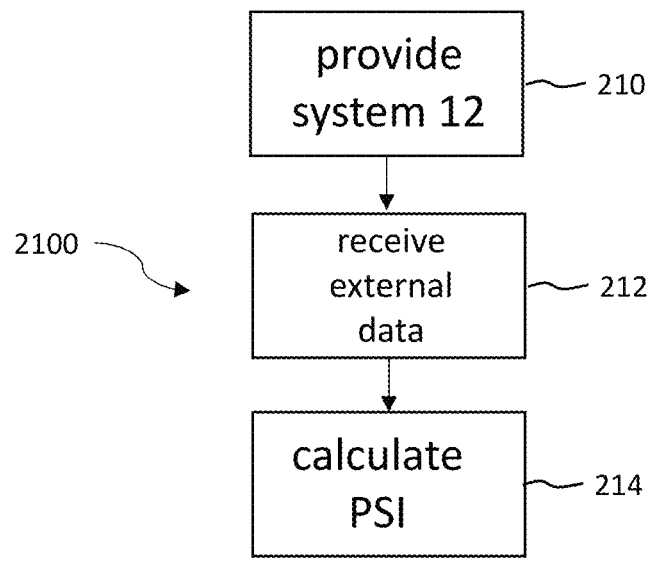
FIG. 19 is a flowchart diagram of an exemplary embodiment of a method for measuring passenger satisfaction.

FIG. 19 shows an exemplary embodiment of a method 2100 for measuring passenger satisfaction of passenger 14. In block 210, a system 12 (see FIGS. 5-6) is provided including processor 18 and a communication node 34. In block 212, communication node 34 communicates with external device 36 to receive information such as traffic data, weather data, passenger social data, passenger calendar data, or destination data. In block 214, process 18 modifies the passenger satisfaction index PSI based on the traffic data, weather data, passenger social data, passenger calendar data, or destination data.

Figure 20:
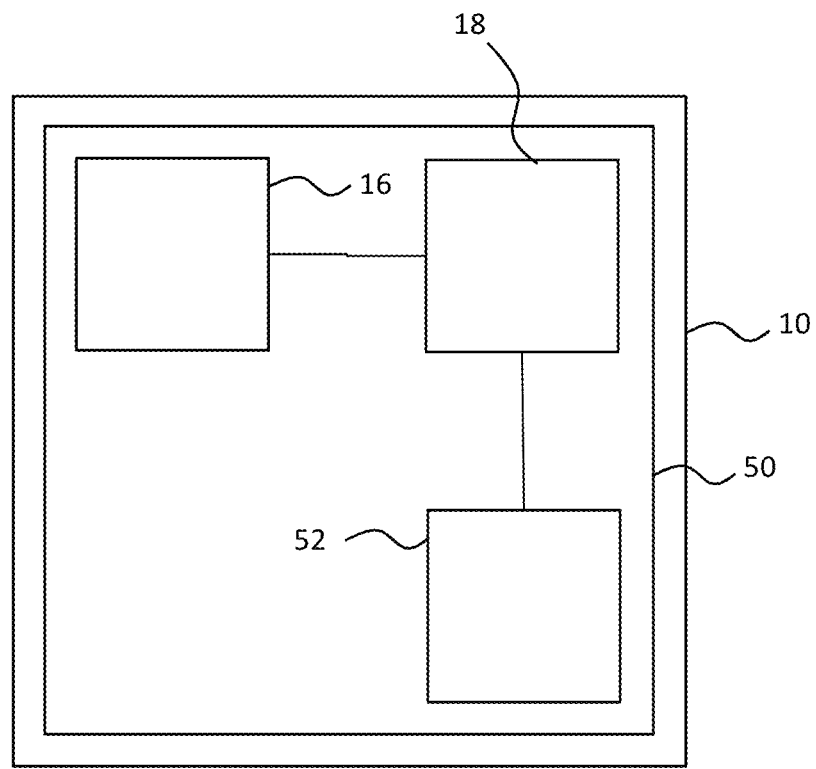
FIG. 20 is a schematic diagram illustrating an exemplary embodiment of a system for modifying driving behavior of an autonomous vehicle based on passenger satisfaction.

In accordance with an exemplary embodiment, FIG. 20 shows a system 50 for modifying driving behavior of an autonomous vehicle 10 based on passenger satisfaction. System 50 may include first sensor 16, processor 18, and automated driving system 52. First sensor 16 and processor 18 may be similar to the structures described in detail herein. Additionally, processor 18 may be operably connected to automated driving system 52 and structured to control automated driving system 52. Automated driving system 52 may include or be operably connected to various controllers and sensors for detecting a driving environment and controlling speed, acceleration, braking, and steering of the autonomous vehicle 10 based on a vehicle path plan calculated by processor 18. The vehicle path plan may include a series of maneuvers planned for autonomous vehicle 10 based on a desired destination and the local driving environment. In other words, automated driving system controls systems such as braking, acceleration, and steering to operate the autonomous vehicle. Processor 18 may be further structured to control the automated driving system 52 to modify driving behavior in response to the passenger satisfaction index PSI satisfying a first condition. Passenger satisfaction index PSI may be calculated as described in detail herein.

The first condition may be a predetermined level of passenger dissatisfaction. To satisfy the first condition, the calculated passenger satisfaction index may need to exceed a predetermined threshold. Processor 18 may be structured so as to, in response to passenger 14 exhibiting the predetermined level of passenger dissatisfaction, control automated driving system 52 to increase deliberateness of the driving behavior of autonomous vehicle 10. In other words, processor 18 controls automated driving system 52 to control the driving behavior to drive in a more careful manner, so as to ease the dissatisfaction of passenger 14.

Deliberateness of the driving behavior of vehicle 10 may be varied in a variety of ways. For example, a magnitude of maximum acceleration of vehicle 10 may be reduced from a baseline value. In words, processor 18 will control automated driving system 52 such that autonomous vehicle 10 will accelerate and decelerate more gradually, so as to decrease anxiety and frustration of passenger 14 and increase trust in the automated vehicle 10. Additionally, increasing deliberateness of the driving behavior of vehicle 10 may include reducing overall vehicle speed.

Figure 21:
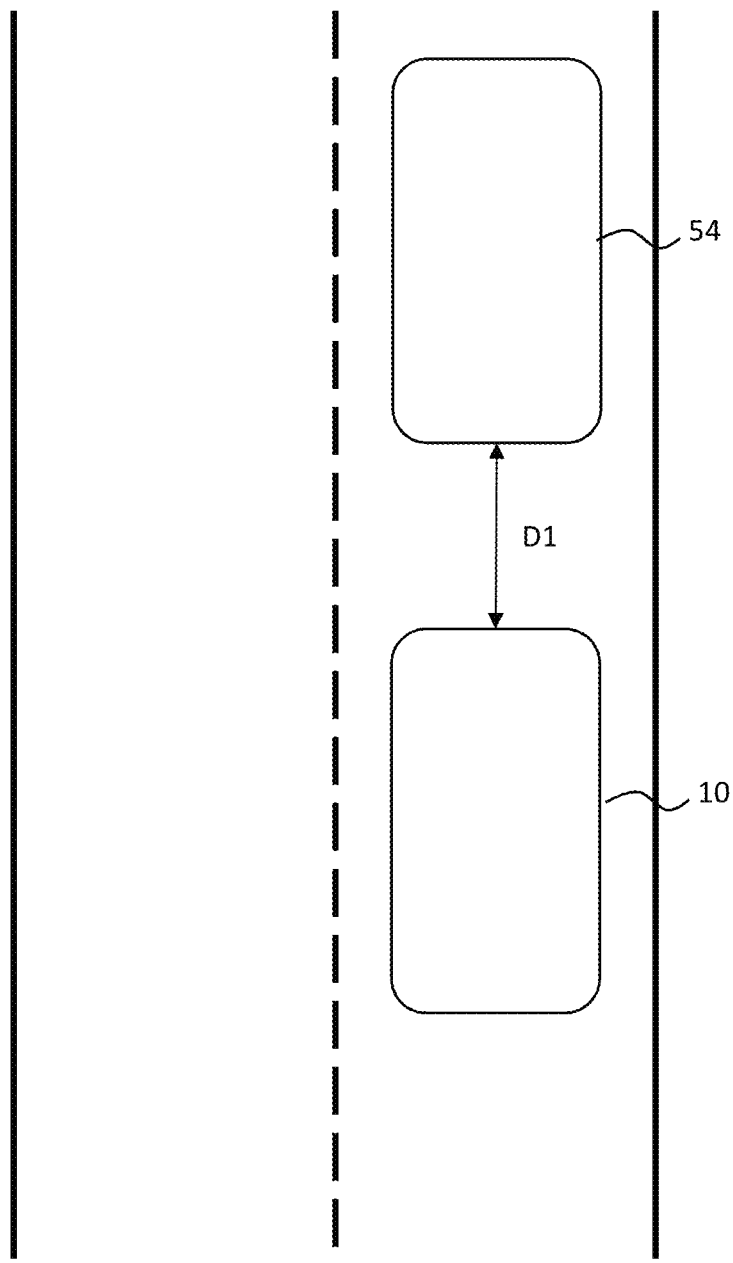
FIG. 21 is an exemplary embodiment illustrating a modification of driving behavior.
Figure 22:
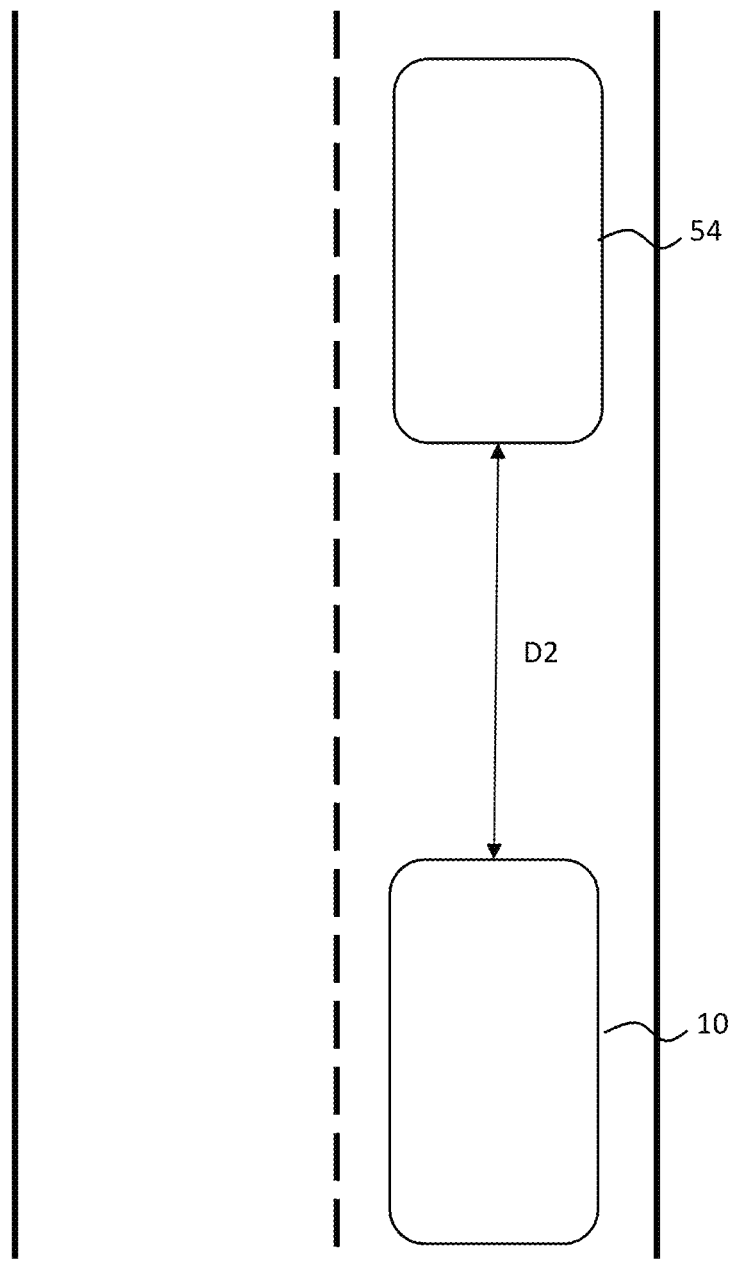
FIG. 22 is an exemplary embodiment illustrating a modification of driving behavior.

Deliberateness may also be increased by controlling automated driving system 52 to maintain a greater distance between autonomous vehicle 10 and nearby or proximate objects. FIG. 21 shows an exemplary embodiment of a baseline driving behavior in which autonomous vehicle 10 maintains a predetermined following distance D1 from second vehicle 54. However, if the passenger satisfaction index PSI satisfies the predetermined level of dissatisfaction, then processor 18 may control automated driving system 52 to maintain a second following distance D2 that is larger than following distance D1, as seen in FIG. 22. The larger following distance D2 may ease frustration and anxiety of passenger 14 and increase trust in autonomous vehicle 10. In similar fashion, processor 18 may control automated driving system 52 to keep a larger distance from other objects such as pedestrians or bicyclists. Processor 18 may further control automated driving system 52 to decrease speed when a distance between autonomous vehicle 10 and a nearby object is less than a predetermined threshold. For example, if autonomous vehicle 10 gets too close to a pedestrian or bicyclist, processor 18 can control automated driving system 18 to further reduce speed.

Overall, increasing the deliberateness of the driving behavior is meant to increase the overall carefulness, caution, and courtesy with which automated vehicle 10 is being operated, in order to decrease anxiety and frustration of passenger 14 and increase trust in autonomous vehicle 10.

Figure 23:
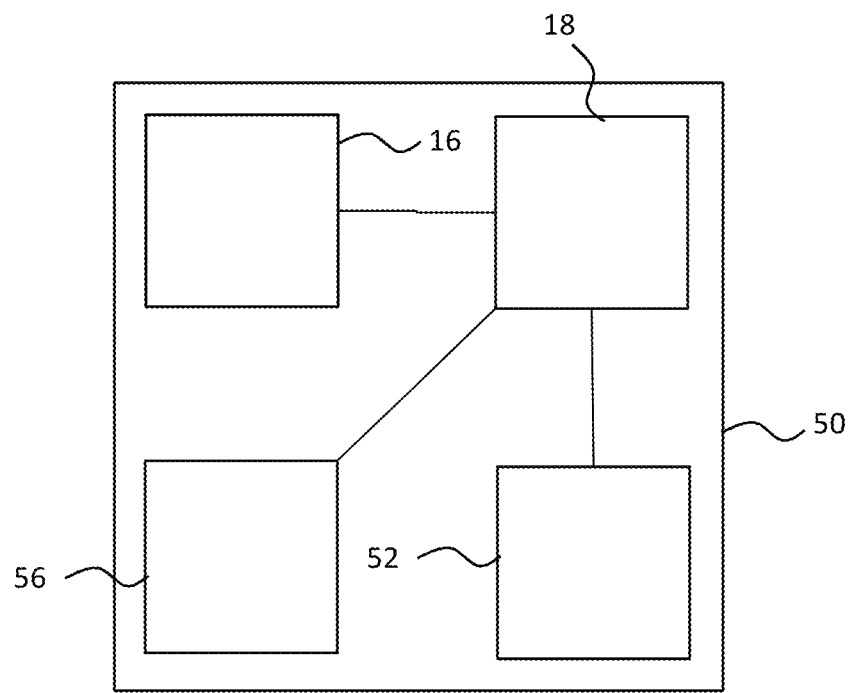
FIG. 23 is a schematic diagram illustrating an exemplary embodiment of a system for modifying driving behavior of an autonomous vehicle based on passenger satisfaction.

FIG. 23 illustrates another exemplary embodiment of the system for modifying driving behavior of an autonomous vehicle. In FIG. 23, system 50 may include a display 56 operably coupled to processor 18. Processor 18 may control display 56 to notify passenger 14 of an upcoming change in driving behavior of autonomous vehicle 10. For example, display 56 may display a notification that vehicle speed is being changed, that following distance is being changed, that a lane change is being made, etc. In this way, display 56 informs passenger 56 that autonomous vehicle is responding to potential concerns of passenger 14, thereby further increasing the trust and confidence of passenger 14 in autonomous vehicle 10.

Figure 24:
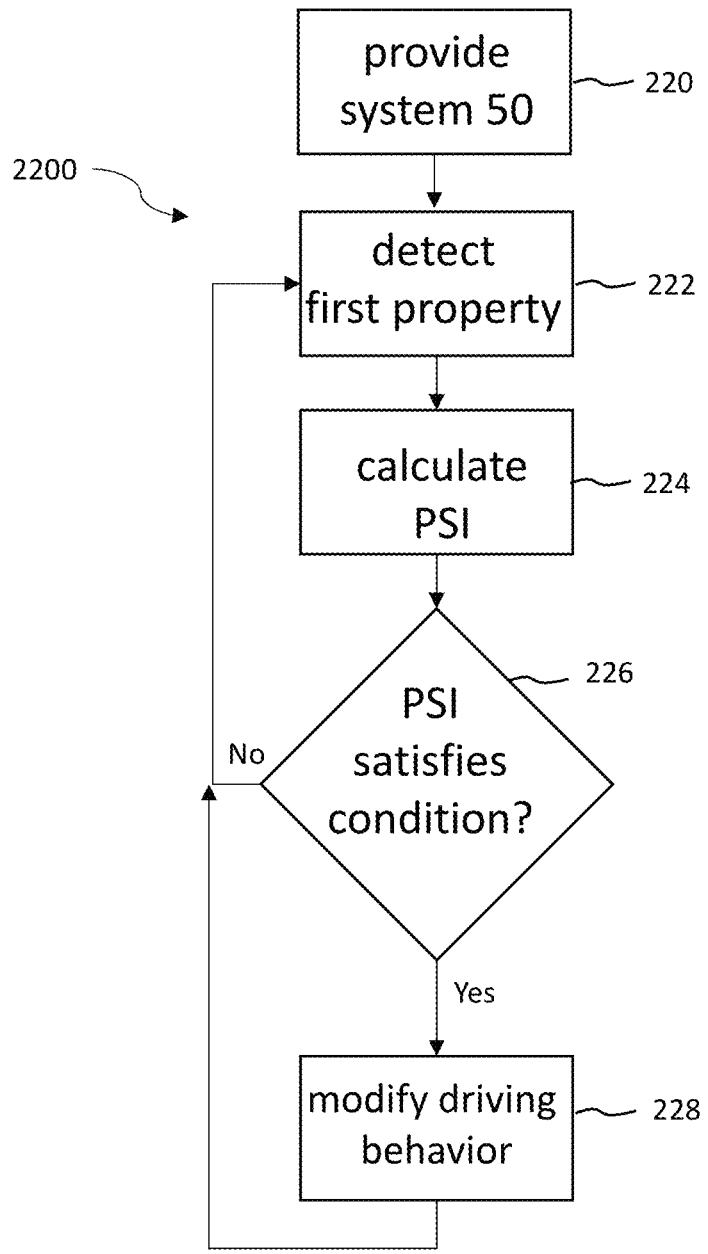
FIG. 24 is a flowchart diagram of an exemplary embodiment of a method for modifying driving behavior of an autonomous vehicle based on passenger satisfaction.

In accordance with an exemplary embodiment, FIG. 24 shows a method 2200 for modifying driving behavior of an autonomous vehicle based on passenger satisfaction of passenger 14. In block 220, a system 50 is provided comprising first sensor 16, processor 18, and automated driving system 52. In block 222, first sensor 16 is used to detect a first property of passenger 14. In block 224, processor 18 calculates passenger satisfaction index PSI based on the first property detected by first sensor 16. In block 226, it is determined whether the passenger satisfaction index PSI satisfies a first condition. If the passenger satisfaction index PSI does satisfy the first condition ("Yes" in block 226), then the method proceeds to block 228. If the passenger satisfaction index PSI does not satisfy the first condition ("No" in block 226), then the method returns to block 222 to continue detecting the first property of passenger 14. In block 228, processor 18 controls automated driving system 52 to modify driving behavior of autonomous vehicle 10. The method may then return to block 222 to continue detecting the first property of passenger 14.

Figure 25:
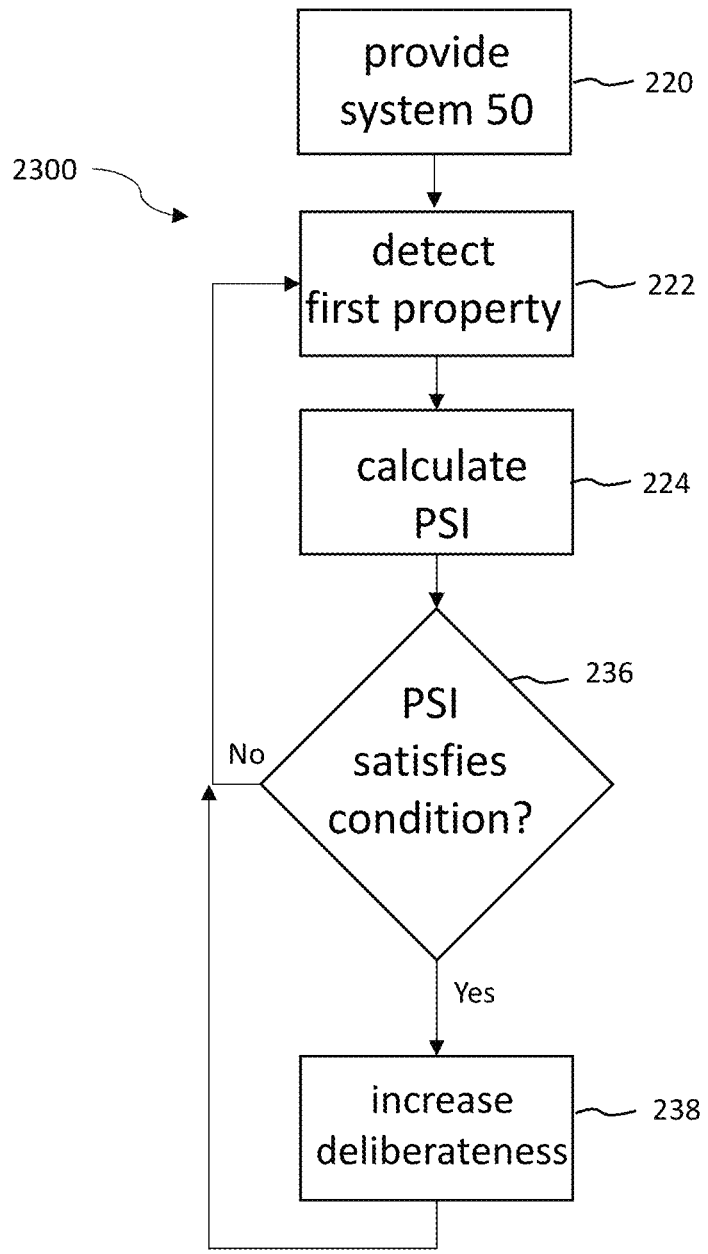
FIG. 25 is a flowchart diagram of an exemplary embodiment of a method for modifying driving behavior of an autonomous vehicle based on passenger satisfaction.

FIG. 25 shows an exemplary embodiment of a method 2300 for modifying driving behavior of an autonomous vehicle based on passenger satisfaction of passenger 14. In block 220, a system 50 is provided comprising first sensor 16, processor 18, and automated driving system 52. In block 222, first sensor 16 is used to detect a first property of passenger 14. In block 224, processor 18 calculates passenger satisfaction index PSI based on the first property detected by first sensor 16. In block 236, it is determined whether the passenger satisfaction index PSI meets a predetermined level of passenger dissatisfaction. If the passenger satisfaction index PSI does meet a predetermined level of passenger dissatisfaction ("Yes" in block 226), then the method proceeds to block 238. If the passenger satisfaction index PSI does not meet the predetermined level of passenger dissatisfaction ("No" in block 226), then the method returns to block 222 to continue detecting the first property of passenger 14. In block 238, processor 18 controls automated driving system 52 to modify driving behavior of autonomous vehicle 10 by increasing deliberateness of the driving behavior of autonomous vehicle 10. The method may then return to block 222 to continue detecting the first property of passenger 14.

Figure 26:
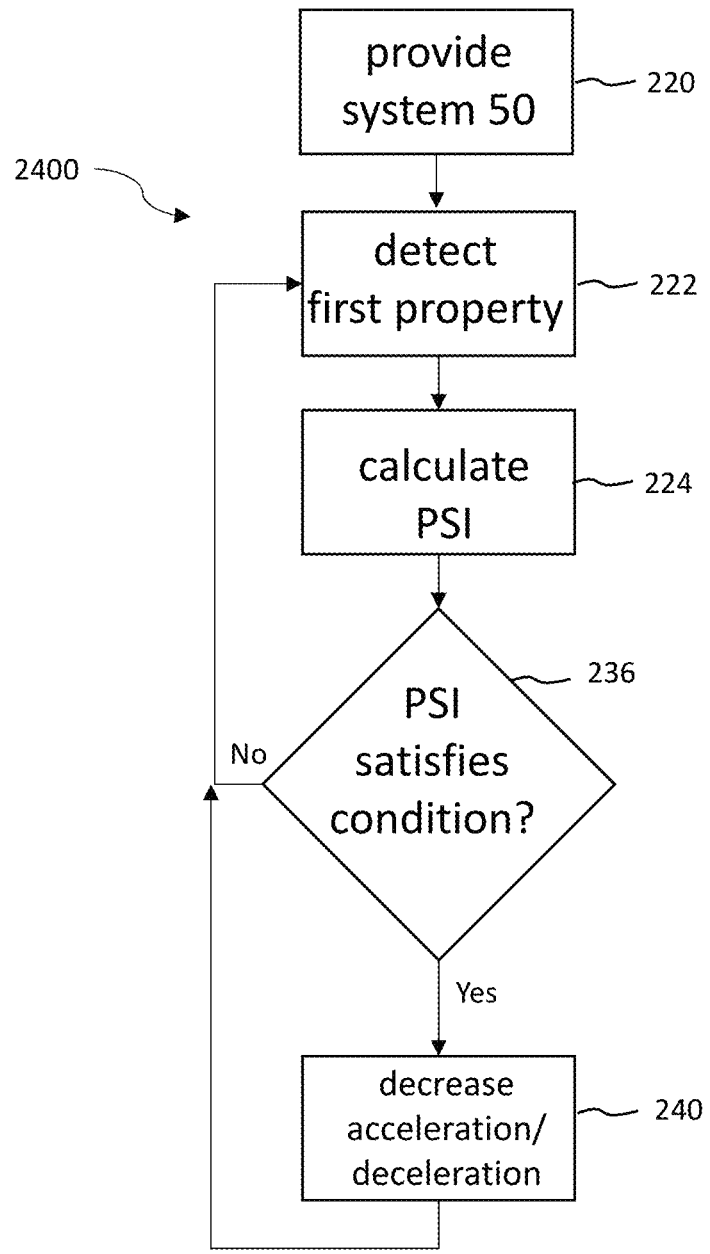
FIG. 26 is a flowchart diagram of an exemplary embodiment of a method for modifying driving behavior of an autonomous vehicle based on passenger satisfaction.

FIG. 26 shows an exemplary embodiment of a method 2400 for modifying driving behavior of an autonomous vehicle based on passenger satisfaction of passenger 14. In block 220, a system 50 is provided comprising first sensor 16, processor 18, and automated driving system 52. In block 222, first sensor 16 is used to detect a first property of passenger 14. In block 224, processor 18 calculates passenger satisfaction index PSI based on the first property detected by first sensor 16. In block 236, it is determined whether the passenger satisfaction index PSI meets a predetermined level of passenger dissatisfaction. If the passenger satisfaction index PSI does meet a predetermined level of passenger dissatisfaction ("Yes" in block 226), then the method proceeds to block 240. If the passenger satisfaction index PSI does not meet the predetermined level of passenger dissatisfaction ("No" in block 226), then the method returns to block 222 to continue detecting the first property of passenger 14. In block 240, processor 18 controls automated driving system 52 to modify driving behavior of autonomous vehicle 10 by decreasing a magnitude of acceleration and/or deceleration of autonomous vehicle 10. The method may then return to block 222 to continue detecting the first property of passenger 14.

Figure 27:
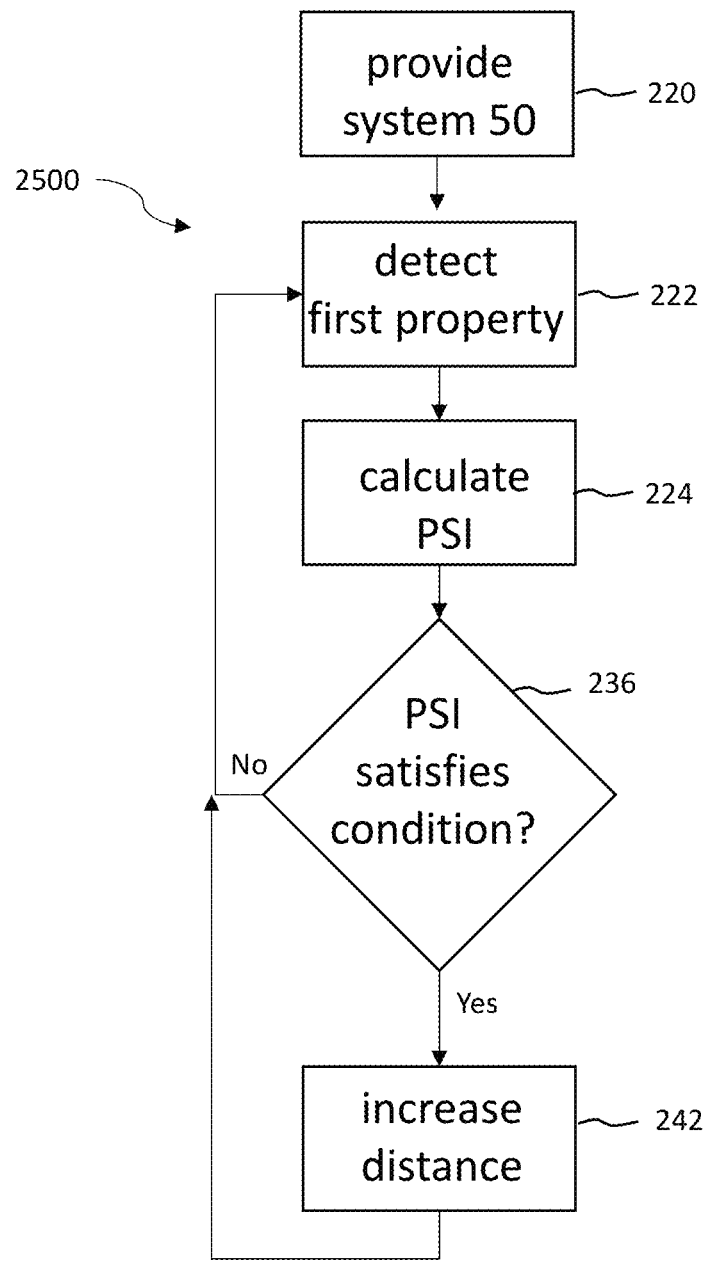
FIG. 27 is a flowchart diagram of an exemplary embodiment of a method for modifying driving behavior of an autonomous vehicle based on passenger satisfaction.

FIG. 27 shows an exemplary embodiment of a method 2500 for modifying driving behavior of an autonomous vehicle based on passenger satisfaction of passenger 14. In block 220, a system 50 is provided comprising first sensor 16, processor 18, and automated driving system 52. In block 222, first sensor 16 is used to detect a first property of passenger 14. In block 224, processor 18 calculates passenger satisfaction index PSI based on the first property detected by first sensor 16. In block 236, it is determined whether the passenger satisfaction index PSI meets a predetermined level of passenger dissatisfaction. If the passenger satisfaction index PSI does meet a predetermined level of passenger dissatisfaction ("Yes" in block 226), then the method proceeds to block 242. If the passenger satisfaction index PSI does not meet the predetermined level of passenger dissatisfaction ("No" in block 226), then the method returns to block 222 to continue detecting the first property of passenger 14. In block 242, processor 18 controls automated driving system 52 to modify driving behavior of autonomous vehicle 10 by increasing a distance between autonomous vehicle 10 and nearby or proximate objects. The method may then return to block 222 to continue detecting the first property of passenger 14.

Figure 28:
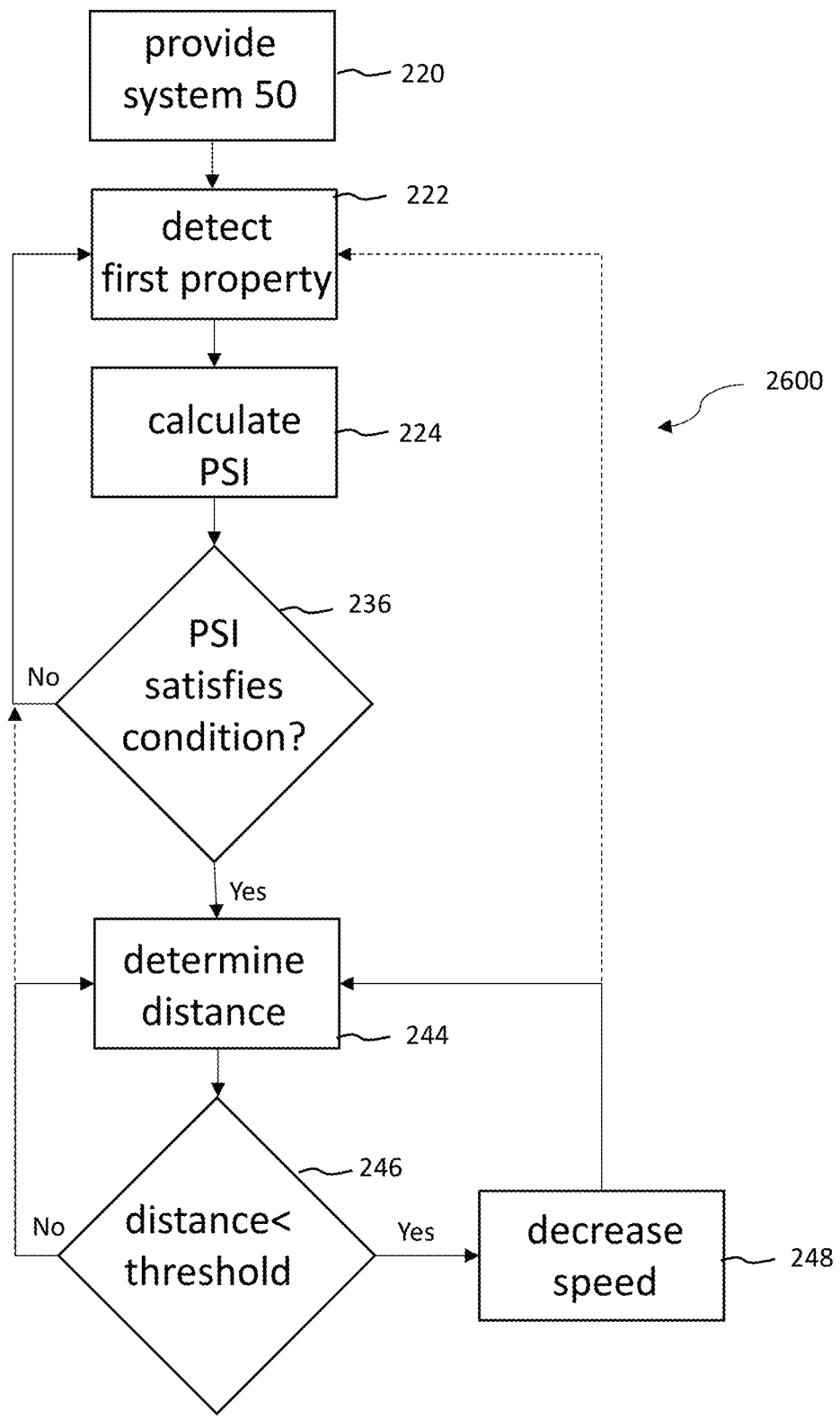
FIG. 28 is a flowchart diagram of an exemplary embodiment of a method for modifying driving behavior of an autonomous vehicle based on passenger satisfaction.

FIG. 28 shows an exemplary embodiment of a method 2600 for modifying driving behavior of an autonomous vehicle based on passenger satisfaction of passenger 14. In block 220, a system 50 is provided comprising first sensor 16, processor 18, and automated driving system 52. In block 222, first sensor 16 is used to detect a first property of passenger 14. In block 224, processor 18 calculates passenger satisfaction index PSI based on the first property detected by first sensor 16. In block 236, it is determined whether the passenger satisfaction index PSI meets a predetermined level of passenger dissatisfaction. If the passenger satisfaction index PSI does meet a predetermined level of passenger dissatisfaction ("Yes" in block 226), then the method proceeds to block 244. If the passenger satisfaction index PSI does not meet the predetermined level of passenger dissatisfaction ("No" in block 226), then the method returns to block 222 to continue detecting the first property of passenger 14. In block 244, a distance to a nearby object is determined. In block 246, it is determined whether the distance to the nearby object is less than a predetermined threshold. If the distance to the nearby object is less than the predetermined threshold ("Yes" in block 246), then the method proceeds to block 248. If the distance to the nearby object is not less than the predetermined threshold ("No" in block 246), then the method returns to block 244 to continue detecting distance to nearby objects. Alternatively, in another exemplary embodiment, the method may return to block 222 to continue detecting the first property of passenger 14 to determine whether further adjustments to driving behavior are necessary (shown as dashed line in FIG. 28). In block 248, processor 18 controls automated driving system 52 to modify driving behavior of autonomous vehicle 10 by decreasing a speed of autonomous vehicle 10. The method may then return to block 244 to continue detecting a distance to nearby objects. Alternatively, in another exemplary embodiment, the method may return to block 222 to continue detecting the first property of passenger 14 to determine whether further adjustments to driving behavior are necessary (shown as dashed line in FIG. 28).

Figure 29:
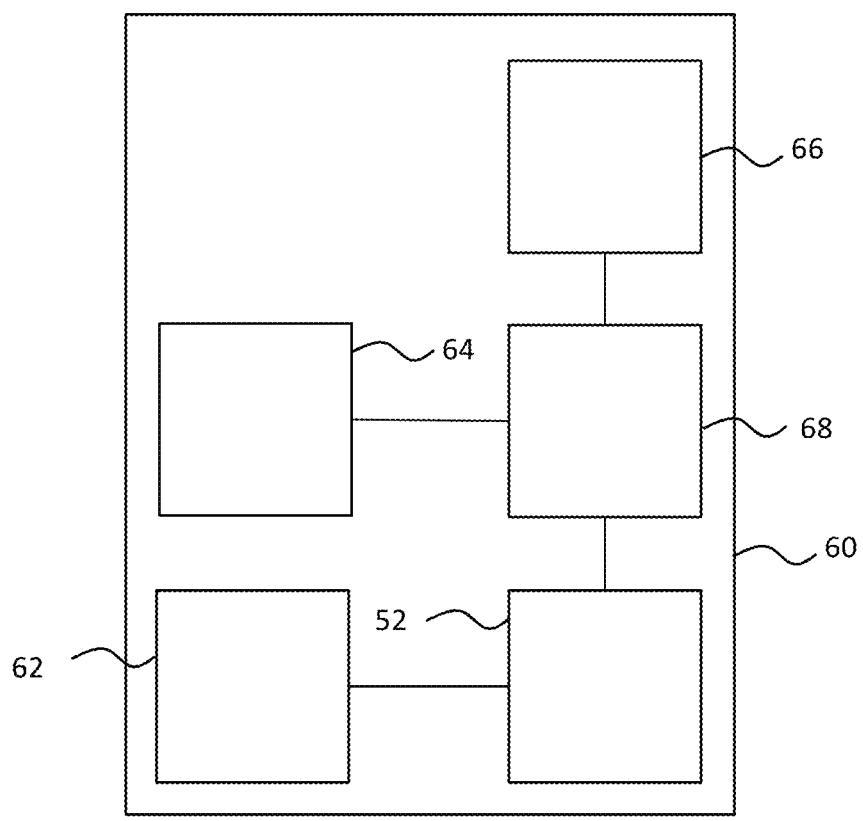
FIG. 29 is a schematic diagram illustrating an exemplary embodiment of a system for increasing passenger satisfaction in operation of an autonomous vehicle.

In accordance with an exemplary embodiment, FIG. 29 shows an embodiment of a system 60 for increasing satisfaction of a passenger 14 in an autonomous vehicle 10 having an automated driving system 52. System 60 may include processor 68, automated driving system 52, first sensor 62, second sensor 64, and display 66. Automated driving system 52 is described in detail herein. Processor 68 is similar to processor 18 described above, with the addition that processor 18 is structured to calculate a vehicle path plan based on input from first sensor 62. Additionally, processor 68 may control display 66 to display a graphical representation of the driving environment of the vehicle and the vehicle path plan.

First sensor 62 may be operably connected to automated driving system 52 and/or processor 68. First sensor 62 may be structured to detect a driving environment of the vehicle, and, as exemplary embodiments, may include a camera, Radio Detection and Ranging (RADAR) system, Light Detection and Ranging (LIDAR) system, or any combination of these systems. First sensor 62 detects the surroundings of autonomous vehicle 10 so that processor 68 is aware of nearby objects and can create or adjust a vehicle path plan accordingly. Second sensor 64 will be discussed in detail below.

Figure 30:
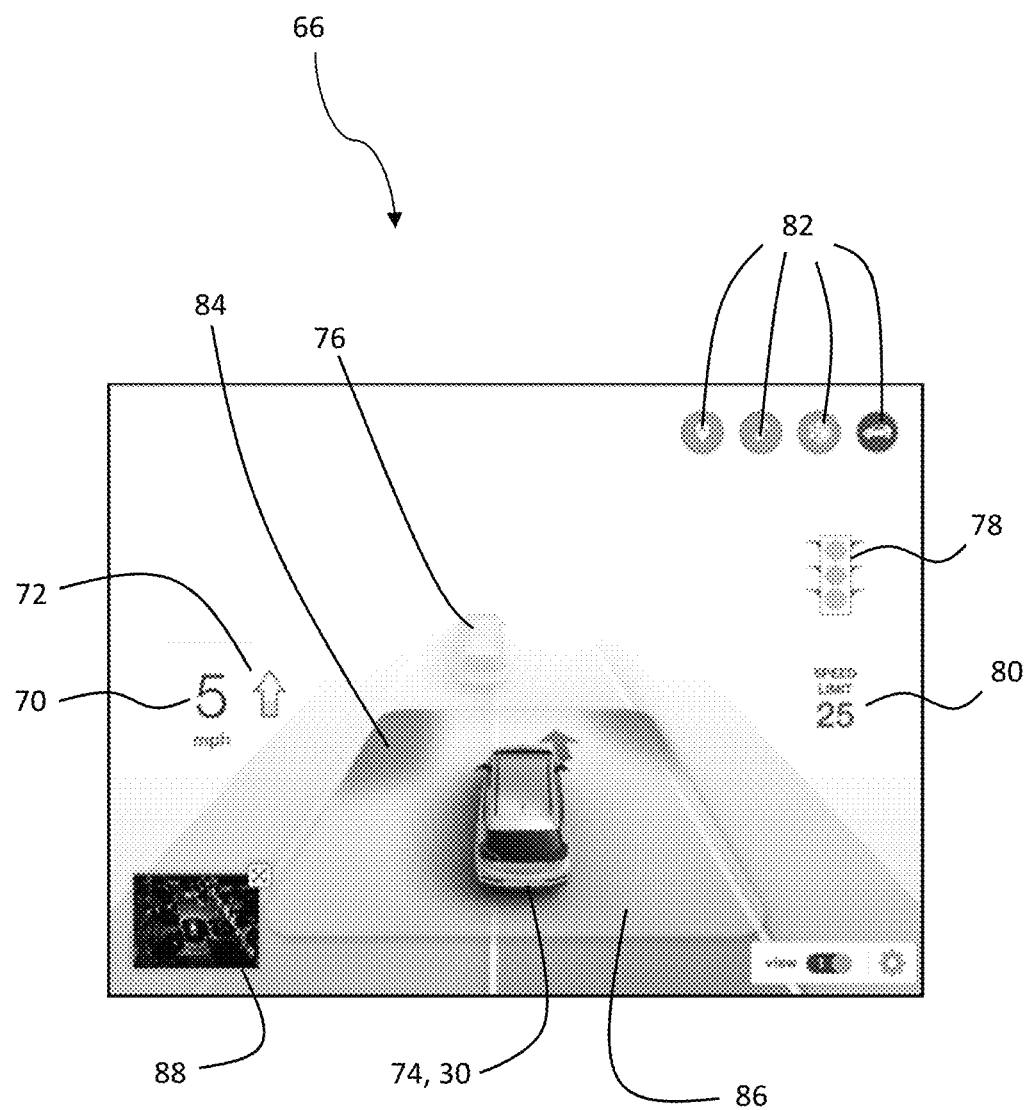
FIG. 30 is a diagram of an exemplary embodiment of a display for increasing passenger satisfaction in operation of an autonomous vehicle.

FIG. 30 shows an exemplary embodiment of display 66 (see FIG. 29). Display 66 may be an LCD screen, LED screen, or other suitable type of display screen, and can be mounted in autonomous vehicle 10 to be visible by passenger 14. Display 66 may also be incorporated into existing display modules used in vehicles for controlling environmental or audio features. Display 66 may also be a touch screen device so that passenger 14 can make inputs by touching display 66.

Display 66 may provide a variety of information to passenger 14. For example, display 66 may show real-time data related to the operation of autonomous vehicle 10, such as vehicle speed 70 and acceleration status 72. In FIG. 30, acceleration status 72 is shown by an arrow indicating a direction of the acceleration, which the magnitude of acceleration being shown by an amount of shading in an arrow icon.

Display 66 may further show a stylized icon 74 representing autonomous vehicle 10, and stylized icons 76 to represent a relative position of nearby objects. In FIG. 30, stylized icon 76 shows a vehicle ahead of autonomous vehicle 10. It will be understood that other types of stylized icons could also be used, such as icons for pedestrians, bicyclists, road obstacles, etc. Processor 68 (see FIG. 29) may be structured to classify nearby objects based on information from first sensor 62 or from vehicle-to-vehicle or vehicle-to-infrastructure communication. Display 66 may be further configured to indicate proximity to nearby structures by various levels of shading or color, as shown by shaded region 84. Display 66 may further illustrate a buffer zone 86 to represent a distance maintained between autonomous vehicle 10 and nearby objects by processor 18 and automated driving system 52.

Display 66 may further show icons indicating various features of infrastructure information. In FIG. 30, for example, display 66 may include an icon 78 indicating a stoplight ahead and an icon 80 indicating the local speed limit. However, it will be understood that many types of icons indicating a variety of different traffic and infrastructure conditions may be used. For example, display 66 may display icons representing a yield zone, merging traffic, construction zones, upcoming roundabouts, intersections, one-way streets, tolls, stop signs, school zones, etc.

Display 66 may further show display icons 82. Display icons 82 can be pressed by passenger 14 to configure display 66 or activate other options. Display 66 may further show a LIDAR thumbnail 88 that shows a real-time image of the surroundings as detected by a LIDAR system of autonomous vehicle 10.

Figure 31:
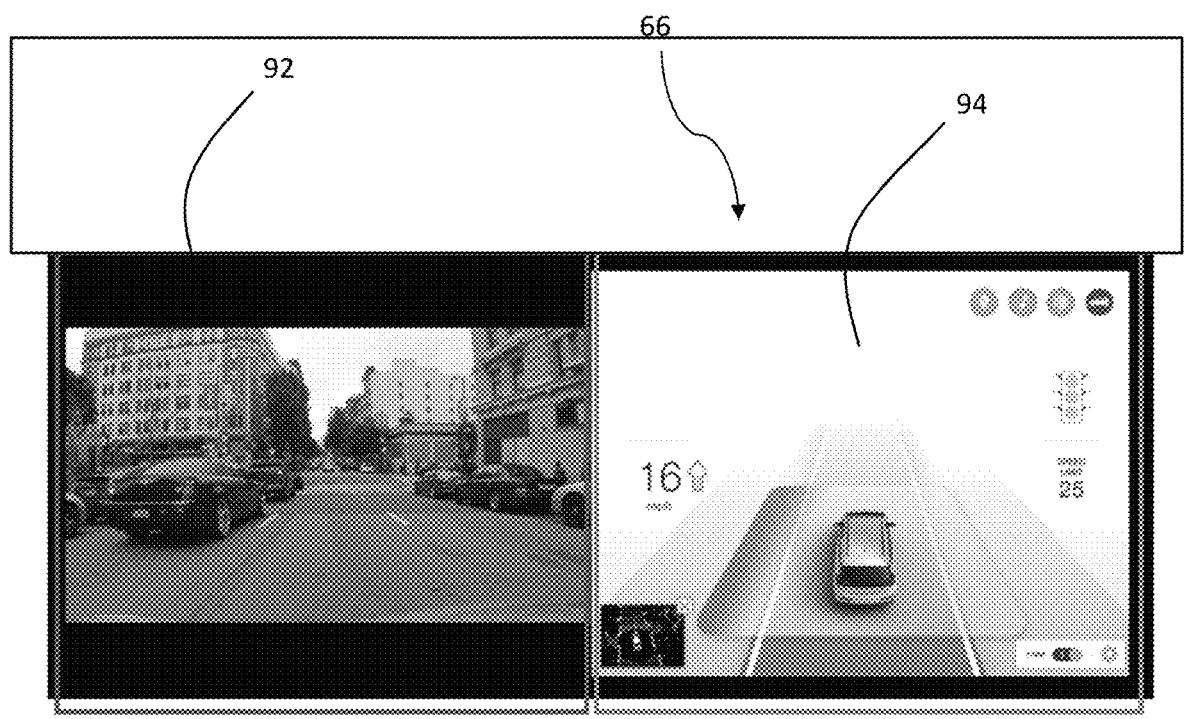
FIG. 31 is a comparison of an exemplary embodiment of a driving environment and an exemplary embodiment of a display.

Overall, display 66 is structured to provide a simplified and easy-to-read graphical representation of the information used by processor 18 and automated driving system 52 to control the vehicle. FIG. 31 shows a comparison between an exterior driving environment 92, and the graphical representation 94 shown on display 66 corresponding to the exterior driving environment 92. Based on this structure, passenger 66 can become easily aware of the information being considered and used by processor 18 and automated driving system 52 to control vehicle 10.

Figure 32:
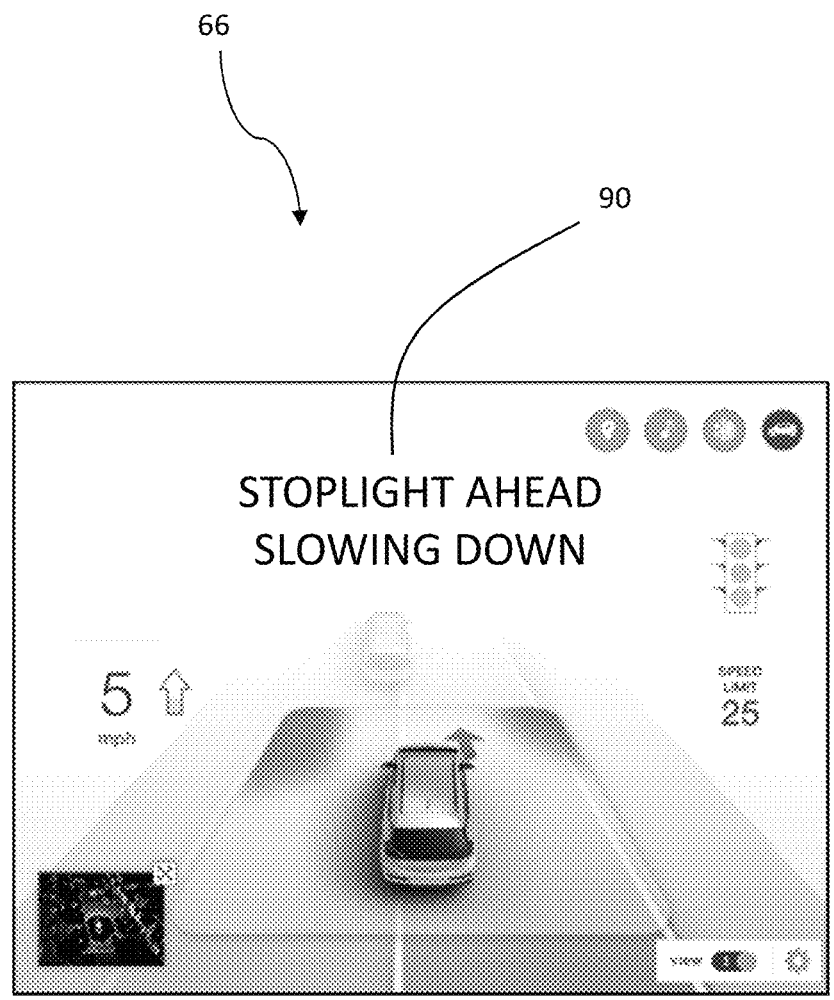
FIG. 32 is a diagram of an exemplary embodiment of a display for increasing passenger satisfaction in operation of an autonomous vehicle.

Display 66 may be further structured to provide information regarding an upcoming maneuver based on the vehicle path plan. FIG. 32 shows an exemplary embodiment in which, based on inputs from first sensor 62, processor 68 may determine that a stoplight is ahead, and accordingly alter the vehicle path plan and control automated driving system 52 to slow autonomous vehicle 10. Display 66 may show a notification 90 so that passenger 14 is aware that autonomous vehicle 10 will decelerate soon. Additionally, system 60 (see FIG. 29) may provide an audio notification of the upcoming maneuver through the speakers of autonomous vehicle 10. In this way, passenger 14 receives foreknowledge of upcoming maneuvers by autonomous vehicle 10, and is not surprised by an unanticipated deceleration. This increases the overall satisfaction and trust of passenger 14 in the operation of autonomous vehicle 10. In contrast, without a notification of upcoming maneuvers, passenger 14 may be surprised by a sudden deceleration, and passenger 14 may feel increased frustration, anxiety, or distrust in the operation of autonomous vehicle 10. While FIG. 32 shows a notification 90 of "STOPLIGHT AHEAD SLOWING DOWN," it will be understood that many different types of notifications are possible. For example, notification 90 may include notifications of upcoming acceleration, turns, lane shifts, passing maneuvers, highway merge/exit, yield maneuver or any other maneuver made by autonomous vehicle 10.

Figure 33:
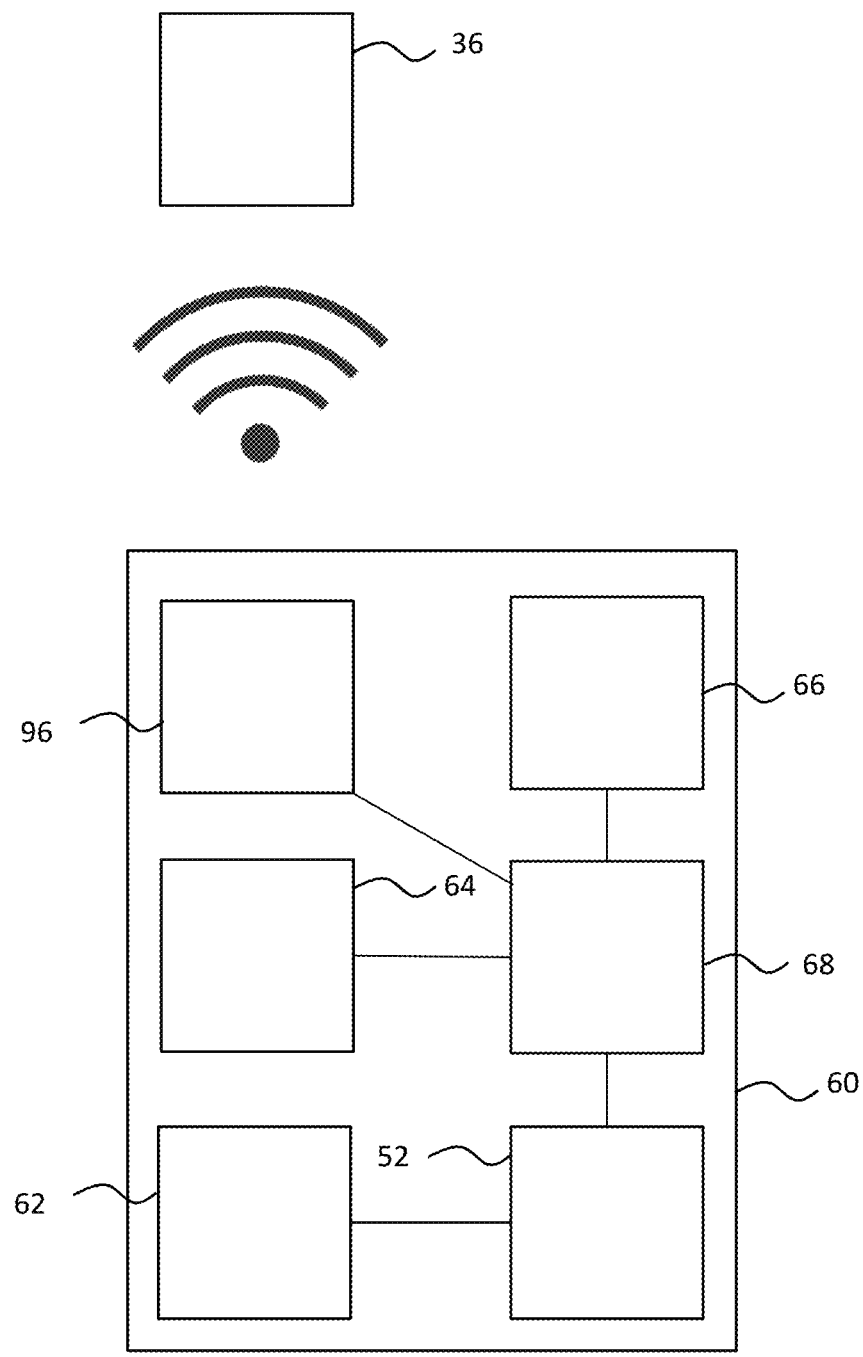
FIG. 33 is a schematic diagram illustrating an exemplary embodiment of a system for increasing passenger satisfaction in operation of an autonomous vehicle.

FIG. 33 shows another exemplary embodiment in which system 60 includes a communication node 96. Communication node 96 may be similar in structure and function to communication node 34 described herein, and communication node 96 may be structured to communicate with external device 36 via wireless communications. Exemplary embodiments of external device 36 are described in detail herein. In particular, external device 36 may be devices provided in local infrastructure such as signs and stoplights to provide traffic and infrastructure information to processor 18, which can be used to display information on display 66 such as that shown by icons 78, 80 in FIG. 30.

Figure 34:
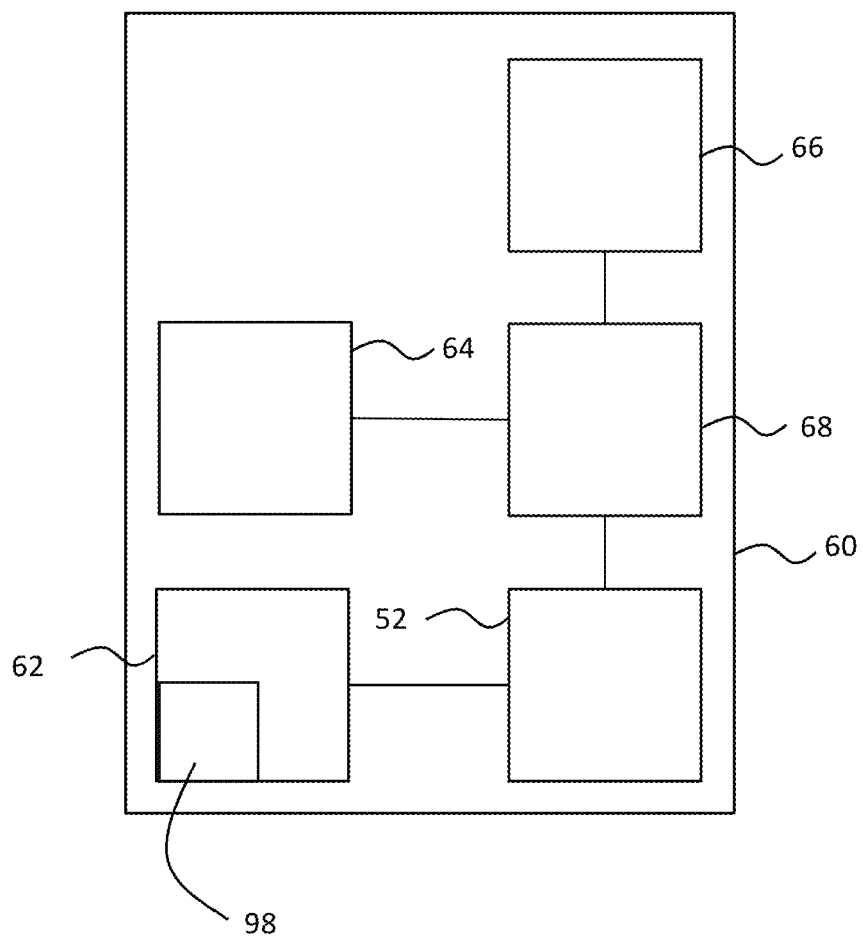
FIG. 34 is a schematic diagram illustrating an exemplary embodiment of a system for increasing passenger satisfaction in operation of an autonomous vehicle.
Figure 35:
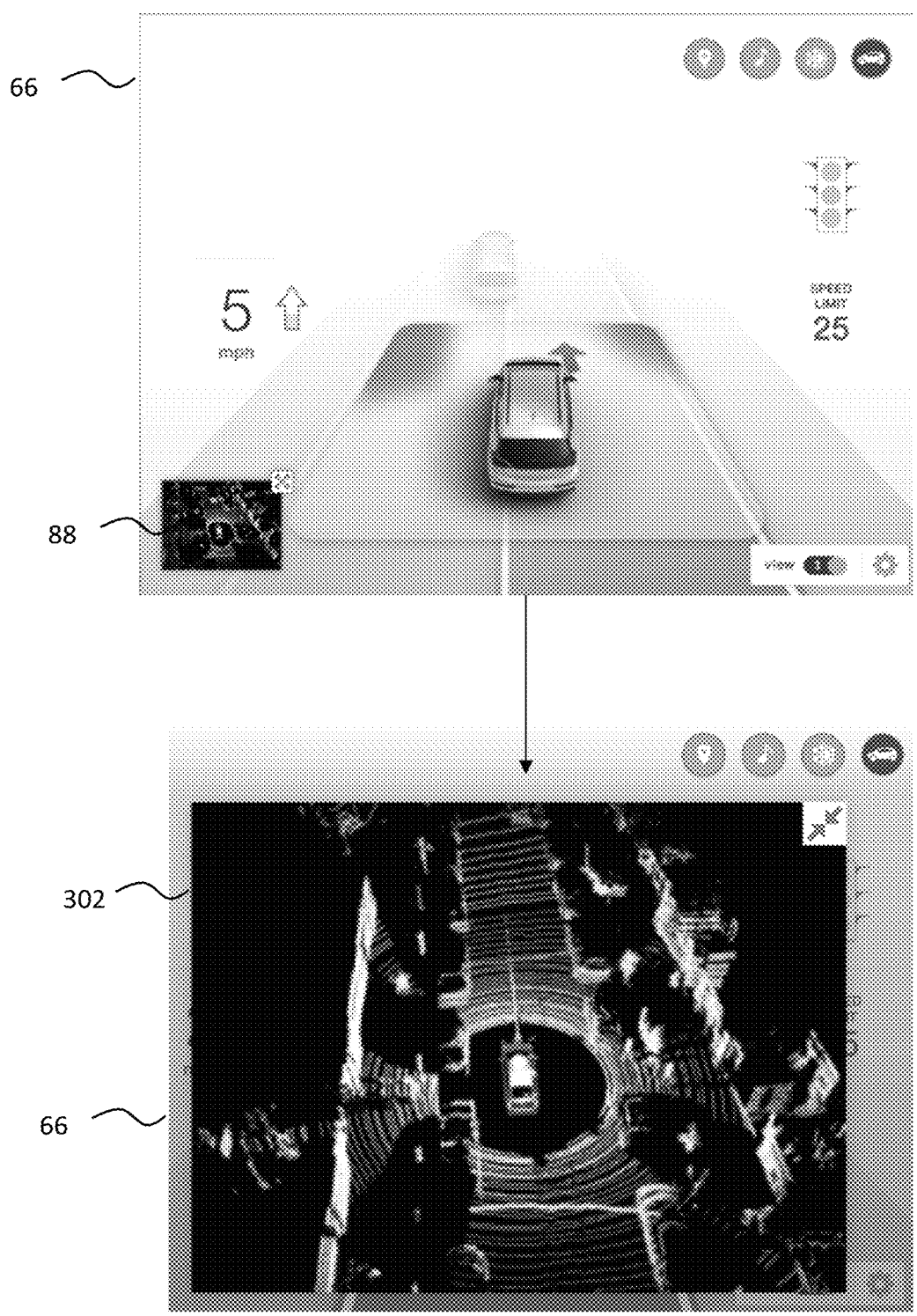
FIG. 35 is a diagram of an exemplary embodiment of a display for increasing passenger satisfaction in operation of an autonomous vehicle.

FIG. 34 shows another exemplary embodiment of system 60 in which first sensor 62 includes LIDAR system 98. LIDAR system 98 may be used for detecting an external driving environment of autonomous vehicle 10, and this information can be used by processor 68 and automated driving system 52 to create and/or modify a vehicle path plan. As shown in FIG. 35, display 66 may be configurable to display from LIDAR system 98. For example, the top view of display 66 in FIG. 35 shows a standard view having LIDAR thumbnail 88. However, in response to an input by passenger 14, display 66 can provide an enlarged LIDAR display 302. This allows passenger 14 to receive a higher level of detail presented by display 66. In other words, display 66 may be configurable to provide varying levels of detail based on comfort and interest of passenger 14.

Figure 36:
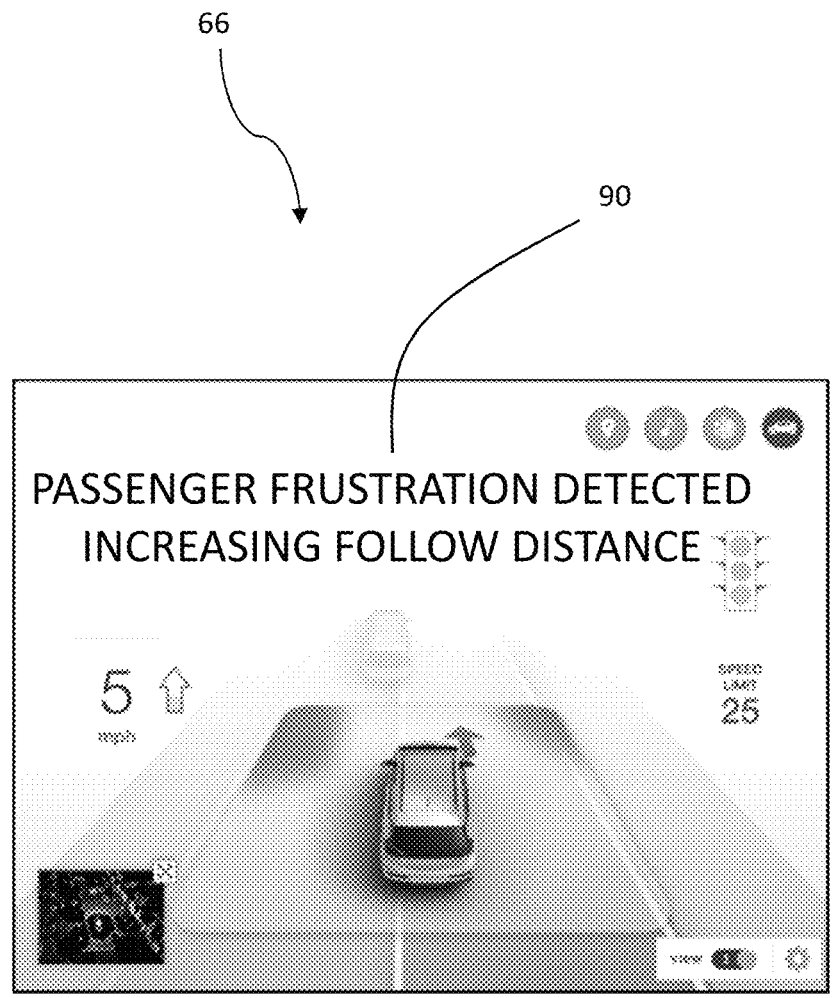
FIG. 36 is a diagram of an exemplary embodiment of a display for increasing passenger satisfaction in operation of an autonomous vehicle.

As noted herein, system 60 may further include second sensor 64 (see FIG. 29, FIG. 33, or FIG. 34). Second sensor 64 may be similar in structure and function to first sensor 16 described in detail herein with reference to FIG. 1 through FIG. 28. In other words, second sensor 64 may be structured to detect a property of passenger 14 as described in detail herein. Similarly, processor 68 may use the property of passenger 14 detected by second sensor 64 to calculate passenger satisfaction index PSI and change driving behavior of autonomous vehicle 10, as described in detail herein. Additionally, if second sensor 64 and processor 68 detect high levels of dissatisfaction in passenger 14, display 66 may be used as a tool to help alleviate passenger satisfaction. For example, if the passenger satisfaction index PSI indicates a predetermined level of passenger dissatisfaction, processor 68 may control display 66 to display more frequent or more detailed notifications 90 regarding upcoming maneuvers as well as provide notifications of modifications made to driving behavior of autonomous vehicle 10. FIG. 36 shows an exemplary embodiment in which display 66 includes a notification 90 informing the passenger that passenger frustration is detected and therefore a following distance is being increased. Thus, system 60 can help to improve satisfaction and trust of passenger 14 in autonomous vehicle 10, thereby enhancing the user experience.

Figure 37:
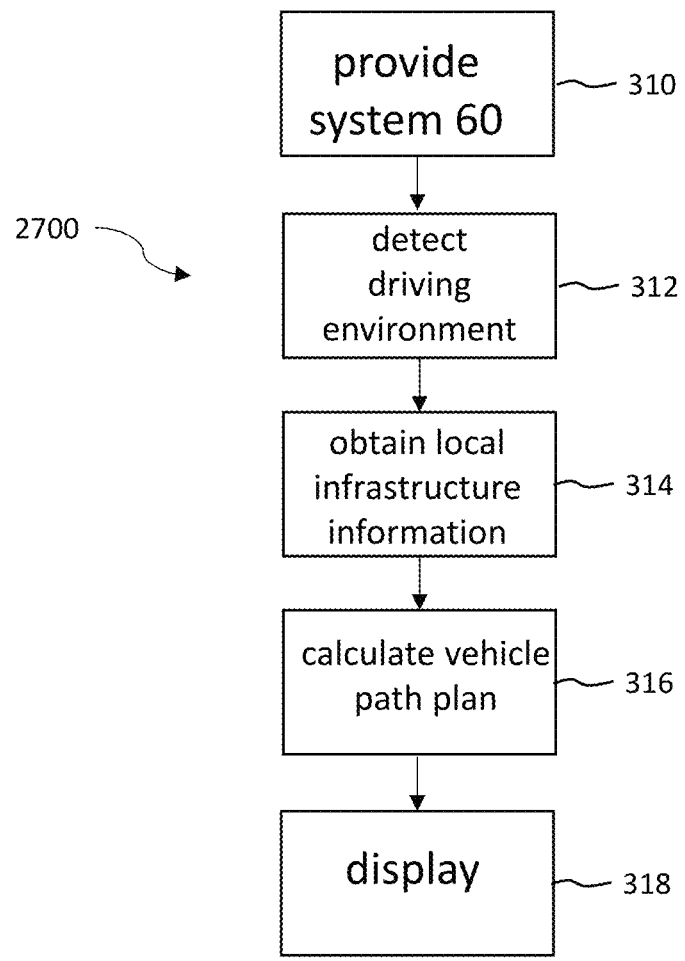
FIG. 37 is a flowchart diagram illustrating an exemplary embodiment of a method for increasing passenger satisfaction in operation of an autonomous vehicle.

In accordance with an exemplary embodiment, FIG. 37 shows a method 2700 for increasing satisfaction of passenger 14 in an autonomous vehicle 10 having an automated driving system 52. In block 310, a system 60 (see FIG. 29) including a first sensor 62, processor 68, and display 66 is provided. In block 312, first sensor 62 detects a driving environment in the vicinity of autonomous vehicle 10. In block 314, local infrastructure information is obtained. As described herein, local infrastructure information may be obtained from external device 36 via communication node 96. In block 316, processor 68 calculates a vehicle path plan based on the driving environment of autonomous vehicle 10 and the local infrastructure information. In block 318, processor 68 controls display 66 to display a graphical representation of the driving environment and the vehicle path plan. As discussed herein with reference to FIG. 30, the graphical representation displayed in block 318 may include real-time data of autonomous vehicle 10 such as speed or acceleration, relative positioning of autonomous vehicle 10 and nearby objects, local infrastructure information, or notification of upcoming maneuvers.

Figure 38:
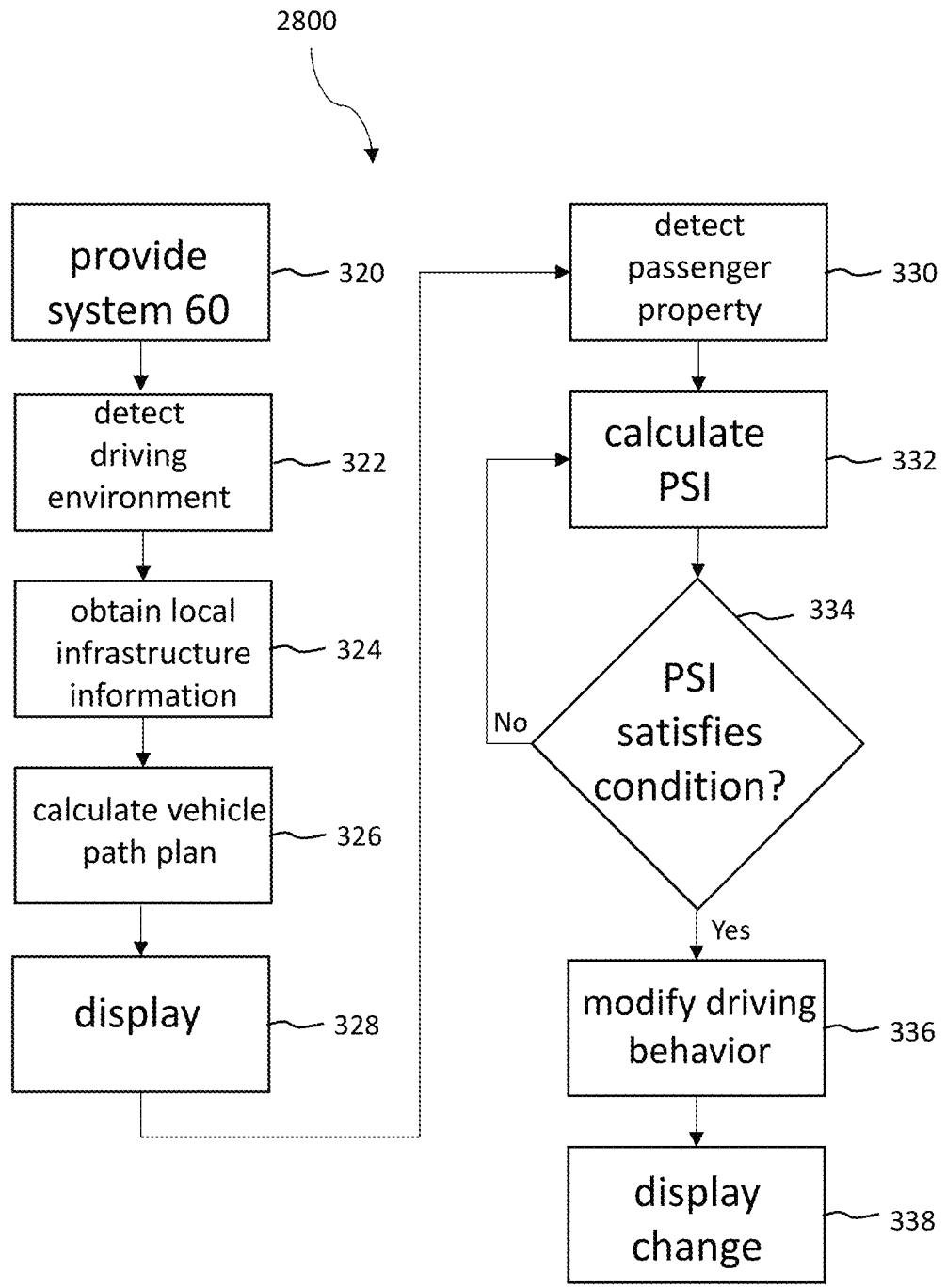
FIG. 38 is a flowchart diagram illustrating an exemplary embodiment of a method for increasing passenger satisfaction in operation of an autonomous vehicle.

FIG. 38 shows an exemplary embodiment of a method 2800 for increasing satisfaction of passenger 14. In block 320, a system 60 (see FIG. 29) including a first sensor 62, a second sensor 64, processor 68, and display 66 is provided. In block 322, first sensor 62 detects a driving environment in the vicinity of autonomous vehicle 10. In block 324, local infrastructure information is obtained. In block 326, processor 68 calculates a vehicle path plan based on the driving environment of autonomous vehicle 10 and the local infrastructure information. In block 328, processor 68 controls display 66 to display a graphical representation of the driving environment and the vehicle path plan. In block 330, second sensor 64 detects a property of passenger 14, as described in detail above. In block, 332, processor 68 calculates a passenger satisfaction index PSI based on the property of passenger 14. In block 334, it is determined whether passenger satisfaction index PSI satisfies a first condition. If passenger satisfaction index PSI does satisfy the first condition ("Yes" in block 334), the method proceeds to block 336. If the passenger satisfaction index PSI does not satisfy the first condition ("No" in block 334), the method returns to block 332 to continue detecting the property of passenger 14. In block 336, processor 68 controls automated driving system 52 to modify a driving behavior of autonomous vehicle 10. Exemplary embodiments of modification of the driving behavior of autonomous vehicle 10 are discussed in detail herein. In block 338, processor 68 controls display 66 to display a notification informing passenger 14 of the change in driving behavior.

Figure 39:
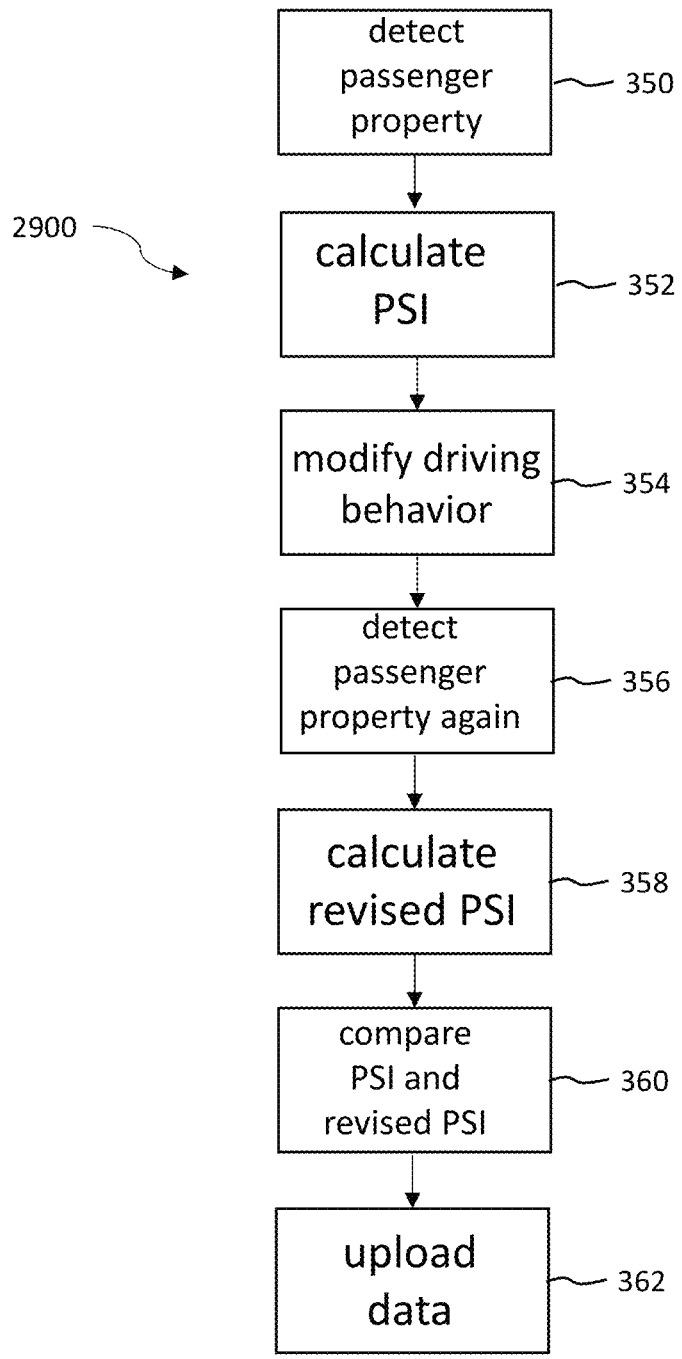
FIG. 39 is a flowchart diagram illustrating an exemplary embodiment of a method for increasing passenger satisfaction in operation of an autonomous vehicle.

The systems and methods described herein may also be used to aid in optimizing measurement of passenger satisfaction, improvement of passenger satisfaction, and modification of driving behavior in response to passenger satisfaction. In an exemplary embodiment, FIG. 39 shows a method 2900 for increasing satisfaction of passenger 14. In block 350, a property of passenger 14 is detected by second sensor 64 (see FIG. 29). In block 352, processor 68 calculates a passenger satisfaction index PSI based on the property of passenger 14. In block 354, processor 68 modifies driving behavior of autonomous vehicle 10. In block 356, the property of passenger 14 is detected again after modification of the driving behavior of autonomous vehicle 10. In block 358, processor 68 calculates a revised passenger satisfaction index PSI based on the new property detected in block 356. In block 360, the revised passenger satisfaction index PSI is compared to the original passenger satisfaction index PSI to determine whether the modification to the driving behavior improved the satisfaction of passenger 14. In block 362, communication node 96 uploads data regarding the original property of passenger 14, the original passenger satisfaction index PSI, the modifications made to the driving behavior, the new property of passenger 14, and the revised passenger satisfaction index PSI to a cloud storage such as a computer 42 accessible via the Internet. The data uploaded by communication node 96 can analyzed by a recurrent neural network and/or using machine learning algorithms in order to determine the effectiveness of the system 60 at both evaluating passenger satisfaction and the effect of modifications of driving behavior on passenger satisfaction. This analysis can be used to improve operation of the system 60 in future operation.

The exemplary embodiments of systems and methods described above result in significant advantages over conventional systems and methods. For example, exemplary embodiments of the present disclosure allow for real-time evaluation and improvement of passenger satisfaction, thereby enhancing a user experience with the autonomous vehicle and mitigating any possible apprehension or lack of trust in autonomous vehicles that may be exhibited.

While the above disclosure has been described with reference to exemplary embodiments, it will be understood by those skilled in the art that various changes may be made and equivalents may be substituted for elements thereof without departing from its scope. In addition, many modifications may be made to adapt a particular situation or material to the teachings of the disclosure without departing from the essential scope thereof. Therefore, it is intended that the present disclosure not be limited to the particular embodiments disclosed, but will include all embodiments falling within the scope thereof.

What is claimed is:

1. A system for increasing satisfaction of a passenger in a vehicle having an automated driving system structured to operate the vehicle, the system comprising:
   a first sensor structured to detect a driving environment of the vehicle, the first sensor being operably coupled to the automated driving system;
   a processor operably coupled to the first sensor and the automated driving system, the processor being structured to calculate a vehicle path plan based on the driving environment of the vehicle and local infrastructure information;
   a display operably coupled to the first sensor, the processor, and the automated driving system, wherein the processor is structured to control the display to display a graphical representation of the driving environment of the vehicle and the vehicle path plan;
   a second sensor structured to detect a first property of the passenger, the second sensor being operably connected to the processor, wherein the processor is structured to calculate a passenger satisfaction index based on the first property of the passenger, to control the automated driving system to modify driving behavior of the vehicle in response to the passenger satisfaction index satisfying a first condition, and to control the display to notify the passenger of a change in driving behavior of the vehicle.

2. The system of claim 1, wherein the graphical representation comprises a current speed of the vehicle, an acceleration status of the vehicle, an indication of nearby objects, and the local infrastructure information.

3. The system of claim 1, wherein the graphical representation comprises an indication of an upcoming maneuver based on the vehicle path plan.

4. The system of claim 1, further comprising a communication node structured to communicate with an external device;
   wherein the communication node is operably coupled to the processor;
   wherein the communication node is structured to receive the local infrastructure information from the external device.

5. The system of claim 1, wherein the first sensor comprises a LIDAR system; and
   the processor is structured to control the display to display a thumbnail of an output of the LIDAR system.

6. The system of claim 5, wherein the processor is structured to control the display to display an enlarged view of the output LIDAR system in response to an input from the passenger.

7. The system of claim 1, wherein the first condition comprises a predetermined level of passenger dissatisfaction; and
   the processor is structured to, in response to the passenger satisfaction index satisfying the predetermined level of passenger dissatisfaction, control the automated driving system to increase deliberateness of the driving behavior of the vehicle.

8. The system of claim 1, wherein the first property comprises a passenger frustration index $I_F$ or a passenger trust index $I_T$.

9. The system of claim 8, wherein the passenger frustration index $I_F$ is a function of a road monitoring duration value, a secondary activity duration value, a multi-task activity transaction value, a side window glance value, or a facial gesture value.

10. The system of claim 8, wherein the passenger frustration index $I_F$ is a function of a galvanic skin response value, a skin temperature value, a verbal valence value, or a facial gesture value.

11. The system of claim 1, further comprising a communication node structured to communicate with an external device; and
   wherein the communication node is operably coupled to the processor;
   wherein the second sensor is a smart device worn by the passenger;
   wherein the communication node is structured to communicate with the smart device to receive the first property; and
   wherein the first property comprises a passenger galvanic skin response, a passenger skin temperature, or a passenger heart rate.

12. The system of claim 1, further comprising a communication node structured to communicate with an external device; and
   wherein the communication node is operably coupled to the processor;
   wherein the communication node is structured to receive traffic data, weather data, passenger social data, passenger calendar data, or destination data from the external device; and
   wherein the processor is structured to modify the passenger satisfaction index based on the traffic data, the weather data, the passenger social data, the passenger calendar data, or the destination data.

13. A method for increasing satisfaction of a passenger in a vehicle having an automated driving system structured to operate the vehicle, the method comprising:
   detecting, with a first sensor, a driving environment of the vehicle;
   obtaining local infrastructure information;
   calculating, with a processor, a vehicle path plan based on the driving environment of the vehicle and the local infrastructure information;
   displaying, on a display, a graphical representation of the driving environment of the vehicle and the vehicle path plan;
   detecting, with a second sensor, a first property of the passenger;
   calculating, with the processor, a passenger satisfaction index based on the first property of the passenger;
   controlling the automated driving system to modify driving behavior of the vehicle in response to the passenger satisfaction index satisfying a first condition; and
   displaying, on the display, a notification of a change in driving behavior of the vehicle.

14. The method of claim 13, wherein the displaying a graphical representation comprises displaying a current speed of the vehicle, an acceleration status of the vehicle, an indication of nearby objects, and the local infrastructure information.

15. The method of claim 13, wherein the displaying the graphical representation comprises indicating an upcoming maneuver based on the vehicle path plan.

16. The method of claim 13, wherein the first condition comprises a predetermined level of passenger dissatisfaction; and
   the method further comprises, in response to the passenger satisfaction index satisfying the predetermined level of dissatisfaction, controlling the automated driving system to increase deliberateness of the driving behavior of the vehicle.

17. The method of claim 13, further comprising communicating with the second sensor via a communication node of the vehicle;
   wherein the second sensor comprises a smart device worn by the passenger;
   wherein the first property comprises a passenger galvanic skin response, a passenger skin temperature, or a passenger heart rate.

18. The method of claim 13, further comprising receiving, via a communication node of the vehicle, traffic data, weather data, passenger social data, passenger calendar data, or destination data from an external device;
   wherein the passenger satisfaction index is modified based on the traffic data, the weather data, the passenger social data, the passenger calendar data, or the destination data.

* * * * *